(12) United States Patent
Sergeant et al.

(10) Patent No.: US 9,044,478 B2
(45) Date of Patent: Jun. 2, 2015

(54) USE OF 1,4-BIS (3-AMINOALKYL) PIPERAZINE DERIVATIVES IN THE TREATMENT OF NEURODEGENERATIVE DISEASES

(75) Inventors: Nicolas Sergeant, Ronchin (FR); Andre Delacourte, Faches-Thumesnil (FR); Patricia Melnyk, Annoeullin (FR); Luc Buee, Templemars (FR)

(73) Assignees: INSTITUT NATIONAL DE LA SANTE ET DE LA RECHERCHE MEDICALE, Paris (FR); UNIVERSITE DU DROIT ET DE LA SANTA-LILLE II, Lille (FR)

(*) Notice: Subject to any disclaimer, the term of this patent is extended or adjusted under 35 U.S.C. 154(b) by 1213 days.

(21) Appl. No.: 11/666,220

(22) PCT Filed: Nov. 8, 2005

(86) PCT No.: PCT/IB2005/053676
§ 371 (c)(1),
(2), (4) Date: Aug. 15, 2007

(87) PCT Pub. No.: WO2006/051489
PCT Pub. Date: May 18, 2006

(65) Prior Publication Data
US 2009/0149464 A1    Jun. 11, 2009

(30) Foreign Application Priority Data
Nov. 10, 2004 (EP) ..................... 04292674

(51) Int. Cl.
A61K 31/495 (2006.01)
C07D 215/12 (2006.01)
C07D 219/08 (2006.01)
C07D 219/12 (2006.01)
C07D 235/30 (2006.01)
C07D 239/26 (2006.01)
C07D 277/28 (2006.01)
C07D 295/027 (2006.01)
C07D 295/13 (2006.01)
C07D 403/12 (2006.01)

(52) U.S. Cl.
CPC ............ *A61K 31/495* (2013.01); *C07D 215/12* (2013.01); *C07D 219/08* (2013.01); *C07D 219/12* (2013.01); *C07D 235/30* (2013.01); *C07D 239/26* (2013.01); *C07D 277/28* (2013.01); *C07D 295/027* (2013.01); *C07D 295/13* (2013.01); *C07D 403/12* (2013.01)

(58) Field of Classification Search
USPC ...................... 514/252.12, 252.13
See application file for complete search history.

(56) References Cited

U.S. PATENT DOCUMENTS

| | | | |
|---|---|---|---|
| 6,248,356 B1 * | 6/2001 | Tracey et al. ................. | 424/464 |
| 2002/0025920 A1 | 2/2002 | Bischoff et al. | |
| 2006/0052416 A1 * | 3/2006 | Dickson et al. .............. | 514/314 |
| 2007/0026527 A1 | 2/2007 | Delacourte et al. | |

FOREIGN PATENT DOCUMENTS

| WO | WO 02/37118 A1 | 5/2002 |
|---|---|---|
| WO | WO 02/096431 A1 | 12/2002 |
| WO | WO 2004/039377 A1 | 5/2004 |
| WO | WO 2004/056800 A1 | 7/2004 |

OTHER PUBLICATIONS

STN Abstract, Accession No. 1952:2759 Document No. 46:2759. R. Hazard, Quarternary ammonium salts of new tetramines-curare effects. Bulletin de la Societe Chimique de France 209-212 (1952).*
Paul Calabresi & Bruce Chabner, Chemotherapy of Neoplastic Diseases, in Goodman & Gilman's The Pharmacologic Basis of Therapeutics 1381, 1388 (10th ed. 2001).*
Barnaby C.H. May, et al, Potent Inhibition of Scrapie Prion Replication in Cultured Cells by Bis-Acridines, 100 PNAS 3416 (Mar. 7, 2003).*
Carsten Korth, et al, Acridine and Phenothiazine Derivatives as Pharmacotherapeutics for Prion Disease, 98 PNAS 9836 (Aug. 14, 2001).*
Sophie Girault, et al, Antimalarial, Antitrypanosomal, and Antileishmanial Activities and Cytotoxicity of Bis(9-amino-6-chloro-2-methoxyacridines): Influence of the Linker, 43 J Med. Chem. 2646 (Jun. 17, 2000).*
Adina Ryckebusch, et al, Synthesis and Antimalarial Evaluation of New 1,4-bis(3-aminopropyl)piperazine Derivatives, 13 Bioorg. Med. Chem. Let. 3783 (2003).*
Adina Ryckebusch, et al, Synthesis and In Vivo Antimalarial Activity of N1-(7-Chloro-4-quinolyl)-1,4-bis(3-aminopropyl)piperazine Derivatives, 46 J Med. Chem. 542 (2003).*
Dickey et al. Exper. Opin. Ther. Targets (2006), 10, 665-676).*
Sacino et al. Acta Neuropathologica Comm, 2013, 1, 1-14.*
Mark R. Emmerling et al., "Phospholipase $A_2$ Activation Influences the Processing and Secretion of the Amyloid Precursor Protein," Biochemical and Biophysical Research Communications, vol. 197, No. 1, pp. 292-297, Nov. 30, 1993.
Rado Nosal et al., "Cationic Amphiphilic Drugs and Platelet Phospholipase $A_2$ ($cPLA_2$)," Thrombosis Research, vol. 105, pp. 339-345, 2002.
Adina Ryckebusch et al., "Synthesis and Antimalarial Evaluation of New 1,4-bis(3-aminopropyl)piperazine Derivatives," Bioorganic & Medicinal Chemistry Letters, vol. 13, pp. 3783-3787, 2003.
Adina Ryckebusch et al., "Synthesis and in Vitro and in Vivo Antimalarial Activity of $N^1$-(7-Chloro-4-quinolyl)-1,4-bis(3-aminopropyl)piperazine Derivatives," Journal of Medical Chemistry, vol. 46, pp. 542-557, 2003.

(Continued)

Primary Examiner — Misook Yu
Assistant Examiner — Kauser M Akhoon
(74) Attorney, Agent, or Firm — Oliff PLC

(57) ABSTRACT

Use of 1,4-bis(3-aminoalkyl)piperazine derivatives as defined in formula I or II for the manufacture of a pharmaceutical composition intended for the treatment of neurodegenerative diseases, related neurodegenerative diseases, developmental diseases or cancer. The instant invention is also directed to some specific 1,4-bis(3-aminoalkyl)piperazine derivatives and pharmaceutical composition including them.

12 Claims, 1 Drawing Sheet

(56) References Cited

OTHER PUBLICATIONS

Beatrice Bonnet et al., "Trypanothione Reductase Inhibition/Trypanocidal Activity Relationships in a 1,4-Bis(3-aminopropyl)piperazine Series," Bioorganic & Medicinal Chemistry, vol. 8, pp. 95-103, 2000.

Adina Ryckebusch et al., "Synthesis and Antimalarial Evaluation of New $N^1$-(7-chloro-4-quinolyl)-1,4-bis(3-aminopropyl)-piperazine Derivatives," Bioorganic & Medicinal Chemistry Letters, vol. 15, pp. 297-302, 2005.

Flipo et al., "Design, synthesis and Antimalarial Activity of Novel, Quinoline-Based, Zinc Metallo-Aminopeptidase Inhibitors." *Bioorganic and Medicinal Chemistry Letters* vol. 13 (2003), p. 2659-2662.

McKetih et al., "Consensus guidelines for the clinical and pathologic diagnosis of dementia with Lewy bodies (DLB): Report of the consortium on DLB international workshop." *Neurology* (1996), vol. 47, p. 1113-1124.

McKeith et al., "Dementia with Lewy bodies." *The Lancet Neurology* (Jan. 2004), vol. 3, p. 19-28.

Emre, "Dementia in Parkinson's disease: cause and treatment." *Current Opinion in Neurology* (2004), vol. 17, p. 399-404.

De Strooper. "Aph-1, Pen-2, and Nicastrin with Presenilin Generate an Active $\gamma$-Secretase Complex." *Neuron* (2003), vol. 38, p. 9-12.

Cao et al., "A Transcriptively Active Complex of APP with Fe65 and Histone Acetyltransferase Tip60." *Science* (Jul. 2001), vol. 293, p. 115-120.

Pardossi-Piquard et al., "Presenilin-Dependent Transcriptional Control of the A$\beta$-Degrading Enzyme Neprilysin by Intracellular Domains of $\beta$APP and APLP." *Neuron* (2005), vol. 46, p. 541-554.

Lichtenthaler et al., "Amyloid at the cutting edge: activation of $\alpha$-secretase prevents amyloidogenesis in an Alzheimer disease mouse model." *The Journal of Clinical Investigation* (2004), vol. 113 No. 10, p. 1384-1387.

Sergeant et al., "Progressive decrease of amyloid precursor protein carboxy terminal fragments (APP-CTFs), associated with tau pathology stages, in Alzheimer's disease," *Journal of Neurochemistry*, vol. 81, 2002, p. 663-672.

Cohen et al., Journal of Pharmaceutical Science, 1974, 63(7), 1068-1072, "Dependence of toxicity on molecular structure: Group theory analysis".

Sanmartin et al., Mini Review in Medicinal Chemistry, 2006, 6(6), 639-650, "Molecular Symmetry: A Structural Property Frequently Present in New Cytotoxic and Proapoptotic Drugs".

* cited by examiner 6 hours
Aβ 1-42 levels
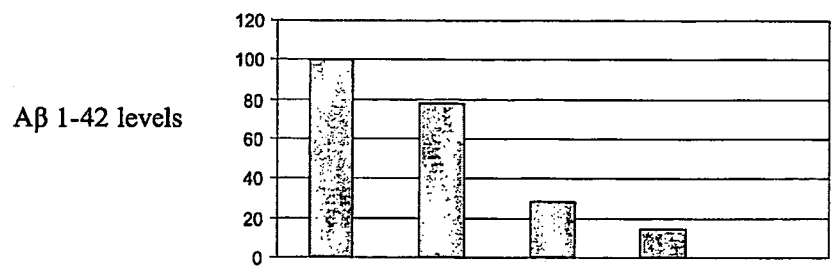
Ctrl  1μM  5μM  1μM  5μM
Compound (6)   Compound
of example 10  of example 4
24 hours
Aβ 1-42 levels
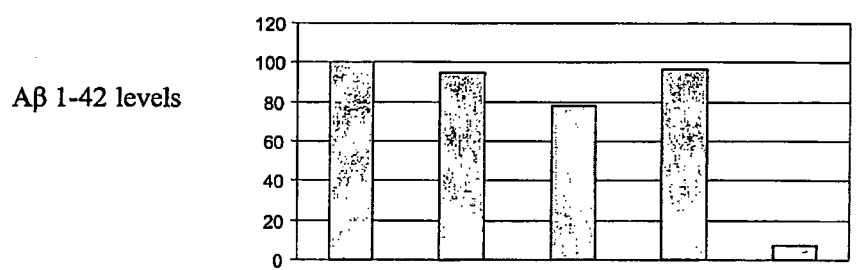
Ctrl  1μM  5μM  1μM  5μM
Compound (6)   Compound
of example 10  of example 4

USE OF 1,4-BIS (3-AMINOALKYL) PIPERAZINE DERIVATIVES IN THE TREATMENT OF NEURODEGENERATIVE DISEASES

The present invention relates to the use of 1,4-bis(3-aminoalkyl)piperazine derivatives of formula (I)

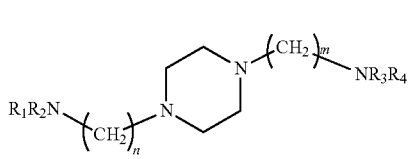

for the manufacture of pharmaceutical compositions intended for the treatment of neurodegenerative diseases, for example a disease distinguished by related disorders with APP dysfunction, and in particular Alzheimer's disease. The present invention also relates to some of said 1,4-bis(3-aminoalkyl) piperazine derivatives to their preparation and their use in therapy.

Alzheimer's disease is a progressive neurological disease that affects brain functions, including short-term memory loss, inability to reason, and the deterioration of language and the ability to care for oneself. An estimated 3% of people between the ages of 65 and 74 have Alzheimer's disease, rising to about half those age 85 and over. Currently, Alzheimer's disease is incurable.

WO 02/37118 discloses means for detecting pathological transformation of the APP protein and their uses in diagnostic and therapeutic applications in degenerative pathologies such as Alzheimer disease.

Some of the compounds of formula (I) are already known, namely various compounds of formula (I) are useful for their antimalarial properties in: "Trypanothione reductase inhibition/trypanocidal activity relationship in a 1,4-bis(3-aminopropyl)piperazine ° series" B. Bonnet et al, *Bioorganic & Medicinal Chermisty* 8 (2000) 95-103, "Synthesis and in vitro and in vivo Antimalarial Activity of N-(7-chloro-4-quinolyl)-1,4-bis(3-aminopropyl)piperazine derivatives" A. Ryckebusch et al, *J. Med. Chem.* (2003), 46, 542-557, "Synthesis and antimalarial evaluation of new 1,4-bis(3-aminopropyl) piperazine derivatives" A. Ryckebusch et al, *Bioorganic & Medicinal Chemistry Letters* 13 (2003) 3783-3787 and in "Design, Synthesis and antimalarial activity of novel quinoline-based, zinc metallo-aminopeptidase inhibitors" M. Flipo et al, *Bioorganic & Medicinal Chemistry Letters* 13 (2003) 2659-2662.

Unexpectedly, the inventors discovered that the molecules according to the present invention could be used to rectify the metabolism of the Amyloid Protein Precursor (APP) on three essential points:

1) increasing the carboxy-terminal fragments of APP (APP-CTFs) which all in common possess the last 50 aminoacids of APP, and especially those having potential physiological activities, such as the g-stubs (APP-CTF alpha) and the g-stubs (APP-CTF gamma or AICD for APP intra cellular domain), 2) decreasing the production of the neurotoxic by-products of APP, i.e. β-amyloid (Aβ) peptides, especially in their form x-42, 3) without modifying the APP expression and in absence of neurotoxicity.

Therefore, the 1,4-bis(3-aminoalkyl)piperazine derivatives as described herein are useful in the treatment of all diseases where a dysfunction of the APP metabolism occurs. The Alzheimer's disease is one said disease.

Accordingly, the present invention relates to the use of a compound represented by the following formula (I)

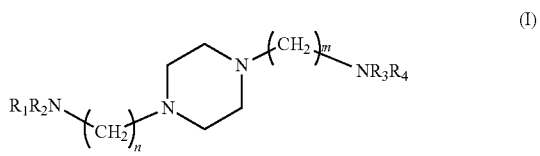

in which n and m are identical or different and independently represent an integer of greater than or equal to 2, particularly ranging from 2 to 8, more preferably ranging from 2 to 6, more particularly being 2, 3 or 4, the resulting hydrocarbon chain optionally comprising one or more heteroatoms selected among oxygen, nitrogen and sulphur, and in which $R_1$, $R_2$, $R_3$ and $R_4$, independently the ones of the others, represent a hydrogen atom, a ($C_1$-$C_7$)alkyl group, straight or branched, saturated or unsaturated, a ($C_1$-$C_7$)alkylcarbonyl group, an aryl group, an aralkyl group, where the aryl group is attached to a ($C_1$-$C_4$)alkylene bridging moiety, a heteroaryl group, where each ($C_1$-$C_7$)alkyl group can be possibly substituted by one or more identical or different groups chosen among a halogen, the cyano group, the hydroxy group, the nitro group, the amino group, a ($C_1$-$C_7$)alkylamino group, a ($C_1$-$C_7$) alkoxy group, a terbutoxycarbonylamino group, a HO—($C_1$-$C_8$)alkyl-group, a $H_2N$—($C_1$-$C_9$)alkyl-group, a HO—(C=O)— group, a ($C_1$-$C_8$)alkyl-O—(C=O)— group, a ($C_1$-$C_8$)alkyl-(C=O)— group, a ($C_1$-$C_8$)alkyl-(C=O)—($C_1$-$C_8$) alkyl-group, a $HSO_3$($C_1$-$C_8$)alkyl-group, a $H_2N$—(C=O)— group and a $H_2N$—(C=O)—$C_1$-$C_8$)alkyl-group, where the aryl group is selected among the groups benzyl, phenyl, biphenyl, anthryl, phenylbenzyl, fluorenyl, naphtyl, dihydronaphtyl, tetrahydronaphtyl, indenyl and indanyl, where the heteroaryl group is an aromatic monocycle, an aromatic bicycle, an aromatic tricycle, or a bicycle or a tricycle of which one or two of the cycles is aromatic and the other cycle(s) is or are partially hydrogenated, from $C_5$ to $C_{14}$ comprising within the cyclic system one, two or three heteroatoms, identical or different, selected among oxygen, nitrogen and sulphur, and where each one of these aryl or heteroaryl groups comprises possibly one or more substitutions, identical or different, chosen among a halogen, the hydroxy group, a ($C_1$-$C_7$) alkyl group, a ($C_1$-$C_7$)alkoxy group, a ($C_7$-$C_{13}$) arylalkoxy group, the cyano group, the nitro group, the amino group, a ($C_1$-$C_7$)alkylamino group, a HO—($C_1$-$C_8$)alkyl-group, a $H_2N$—($C_1$-$C_8$)alkyl-group, a HO—(C=O)— group, a ($C_1$-$C_8$)alkyl-O—(C=O)— group, a ($C_1$-$C_8$)alkyl-(C=O)— group, a ($C_1$-$C_8$)alkyl-(C=O)—($C_1$-$C_8$)alkyl-group, a $HSO_3$ ($C_1$-$C_8$)alkyl-group, a $H_2N$—(C=O)— group and a $H_2N$—(C=O)—($C_1$-$C_8$)alkyl-group, where ($R_1$ and $R_2$) and/or ($R_3$ and $R_4$), independently of one another, can possibly form an aromatic or partially or totally hydrogenated $C_4$ to $C_{14}$ monocycle, optionally comprising within the cyclic system one, two or three heteroatoms, identical or different, selected among oxygen, nitrogen and sulphur, provided that at most two of the radicals chosen among $R_1$, $R_2$, $R_3$ and $R_4$ simultaneously represent a hydrogen atom and that ($R_1$ and $R_2$) or ($R_3$ and $R_4$) do not simultaneously represent a hydrogen atom, or their salts with pharmaceutically acceptable acids, for the manufacture of a pharmaceutical composition intended for the treatment of neurodegenerative diseases, related neurodegenerative diseases, developmental diseases or cancer.

In one particular variant of the present invention the heteroaryl group is different from an acridin group or an acridin derivative. In another variant the heteroaryl group is different from an aromatic tricycle.

The use of derivatives of formula (I) is more particularly intended for the treatment of neurodegenerative diseases or related neurodegenerative diseases where APP and its catabolic products are a cause or a risk factor for the development of the pathology. The derivatives of formula (I) can be used for treatment or prevention. Among neurodegenerative diseases Alzheimer's disease, Down syndrome, amyloid angiopathies, dementia with Lewy bodies and Parkinson's disease may be cited. Indeed, for this two last diseases, important amyloid deposits are always observed in the neocortex of patients with sporadic DLB (Dementia with Lewy Body), and DLB is considered as a continuum of PD (Parkinson's Disease) (McKeith I G et al. Consensus guidelines for the clinical and pathologic diagnosis of dementia with Lewy bodies (DLB): report of the consortium on DLB international workshop. *Neurology* 1996; 47: 1113-1124; McKeith et al Dementia with Lewy bodies. Lancet Neurol 2004; 3:19-28 and Emrle M. Dementia in Parkinson's disease: cause and treatment. *Curr Opin Neurol* 2004; 17:399-404). Therefore, correcting the risk factor due to APP dysfunction is likely to inhibit the conversion of PD into DLB. APP is also a ubiquitous protein, found in all cell types, and a member of a large family involving APP like proteins, or other proteins with a similar catabolism regulated at the surface membrane (Notch, ErbB, N- and E-Cadherine, LRP, Syndecan, . . . ) (De Strooper B. (2003) Aph-1, Pen-2, and Nicastrin with Presenilin generate an active γ-Secretase complex. *Neuron* 38, 9-12). Therefore, the derivatives of formula (I) may also be used for the treatment of pathologies such as cancer. Together, correcting the metabolic cleavage of the C-terminal part of APP and/or APP-like proteins and/or other proteins with structural or conformational homologies with the C-terminal fragments of APP concerns pathologies related to amyloidopathies, tauopathies, synucleopathies as well as developmental diseases and cancer.

The compounds of formula (I) can comprise one or more asymmetrical carbon atoms. They can thus exist in the form of enantiomers or of diastereoisomers. These enantiomers, diastereoisomers, as their mixtures, including the racemic mixtures form part of the invention.

The compounds of the invention may exist in the form of free bases or of addition salts with pharmaceutically acceptable acids.

Suitable pharmaceutically acceptable salts of compounds of formula (I) include base addition salts and where appropriate acid addition salts. Suitable physiologically acceptable base addition salts of compounds of formula (I) include alkali metal or alkaline metal salts such as sodium, potassium, calcium, and magnesium salts, and ammonium salts, formed with amino acids (e.g. lysine and arginine) and organic bases (e.g. procaine, phenylbenzylamine, ethanolamine diethanolamine and N-methyl glucosamine).

Suitable acid addition salts may be formed with organic acid and inorganic acids e.g. hydrochloric acid.

The compounds of formula (I) and or salts thereof may form solvates (e.g. hydrates) and the invention includes all such solvates.

The term $(C_1-C_7)$alkyl as used herein refers to a straight or branched-chain hydrocarbon radical of one to seven carbon atoms and cyclized manifestations thereof unless otherwise indicated. Included within the scope of this term are such moieties as methyl, ethyl, isopropyl, n-butyl, t-butyl, t-butylmethyl, cyclopropyl, N-propyl, pentyl, cyclopentyl, n-hexyl, cyclohexyl, cyclohexylmethyl, 2-ethylbutyl etc.

The term halogen refers to a fluorine, a chlorine, a bromine or an iodine atom.

Fluorine and chlorine are preferred halogen atoms in the framework of the present invention.

The term $(C_1-C_7)$alkoxy refers to alkoxy radical made up of an oxygen radical bearing a saturated straight or branched chain hydrocarbon radical of one to seven carbon atoms. Included within the scope of this term are methoxy, ethoxy, propoxy, n-butoxy, isobutoxy, sec-butoxy, t-butoxy, n-pentoxy, isopentoxy, sec-pentoxy, t-pentoxy . . . and the like.

Among the compound of formula (I) defined above, the compounds for which the use is preferred may be given in details as follows.

A first class of such compounds of formula (I), hereinafter referring to compounds of formula (Ia), is such that $R_1$ and $R_3$ are hydrogen atoms and $R_2$ and $R_4$ are identical and different from a hydrogen atom.

Among this first class of compounds of formula (Ia), the compounds for which the therapeutical use is the most preferred are characterized in that $R_2$ and $R_4$ are selected among a chloroquinolinyl group such as 7-chloroquinolin-4-yl,
a pyridinylmethyl group, such as the pyridin-3-ylmethyl,
a benzyl group possibly substituted one or twice on the phenyl group by a group chosen among an atom of halogen and a methoxy group such as 4-methoxybenzyl, 3,4-dimethoxybenzyl, 4-chlorobenzyl and 4-fluorobenzyl,
a quinolinylmethyl group, such as quinolin-4-ylmethyl, and,
a $(C_1-C_7)$alkyl group, such as cyclopropylmethyl, isobutyl, 2-ethylbutyl and heptyl.

A second class of such compounds of formula (I), hereinafter referring to compounds of formula (Ib), is such that $R_1$ and $R_3$ are hydrogen atoms and $R_2$ and $R_4$ are different and do not represent a hydrogen atom.

Among this second class of compounds of formula (Ib), the compounds for which the therapeutical use is the most preferred are characterized in that $R_2$ is a heteroaryl group such as 7-chloroquinolin-4-yl and the $R_4$ group is a $(C_1-C_7)$alkyl group such as a cyclopropylmethyl group, a isobutyl group, a tertiobutylmethyl group and a cyclohexylmethyl group.

A third class of such compounds of formula (I), hereinafter referring to compounds of formula (Ic), is such that $R_1$ is a hydrogen atom, $R_2$ is different from a hydrogen atom and $R_3$ and $R_4$ are identical and different from a hydrogen atom.

Among this third class of compounds of formula (Ic), the compounds for which the therapeutical use is the most preferred are characterized in that $R_3$ and $R_4$ represent a $(C_1-C_7)$ alkyl group such as an isobutyl group or a cyclopropylmethyl group or form with the nitrogen atom a saturated or unsaturated heterocycle like for example an aziridine, an azetidine, a pyrrolidine, a piperidine or an azepane and $R_2$ represents a group chosen among a benzimdazol group such as the benzimidazol-2-yl group,
a pyrimidin group such as the pyrimidin-2-yl group, a pyrazinyl group such as the pyrazin-2-yl group,
a purin group such as the purin-6-yl group,
a quinolinyl group,
a chloroquinolinyl group such as the 7-chloroquinolin-4-yl group,
an acridin group such as the 6-chloro-2-methoxyacridin-9-yl group,
a benzyl group possibly substituted one or several times on the phenyl group by a group chosen among an atom of halogen and a methoxy group such as the 4-methoxybenzyl group, the 3,4-dimethoxybenzyl group, the 4-chlorobenzyl group and the 4-fluorobenzyl group,
a pyridinylmethyl group such as the pyridin-4-ylmethyl group, and,
a thiazolylmethyl group such as the thiazol-2-ylmethyl group.

In one particular variant of the present invention, $R_2$ is a group different from an acridin or an acridin derivative. In an another variant it is different from an aromatic tricycle.

A fourth class of such compounds of formula (I) hereinafter referring to compounds of formula (Id), is such that $R_1$ is a hydrogen atom and $R_2$, $R_3$ and $R_4$ are different the ones from the others and do not represent a hydrogen atom.

A fifth class of such compounds of formula III hereinafter referring to compounds of formula (II), is such that $R_1$, $R_2$, $R_3$ and $R_4$ are identical.

In the framework of the invention, n and m are possibly identical and more preferably equal to 2 or 3 or 4.

More particularly, these compounds may be chosen among:

1,4-bis{3-[N-(7-chloroquinolin-4-yl)amino] propyl}piperazine,
1,4-bis{3-[N-(pyrid-3-ylmethyl)amino]propyl}piperazine,
1,4-bis{3-[N-(3,4-dimethoxybenzyl)amino] propyl}piperazine,
1,4-bis{3-[4-chlorobenzyl)amino]propyl}piperazine,
1,4-bis{3-[N-(quinol-4-ylmethyl)amino]propyl}piperazine,
1,4-bis{3-[N-(4-methoxybenzyl)amino]propyl}piperazine,
1,4-bis{3-[N-(cyclopropylmethyl)amino]propyl}piperazine,
1,4-bis{3-[N-(isobutyl)amino]propyl}piperazine,
1,4-bis{3-[N-(2-ethylbutyl)amino]propyl}piperazine,
1,4-bis{3-[N-(n-heptyl)amino]propyl}piperazine,
1,4-bis{3-[N-(4-fluorobenzyl)amino]propyl}piperazine,
$N^4$-[3-(4-{3-[(cyclopropylmethyl)amino] propyl}piperazino)propyl]-7-chloroquinolin-4-amine,
$N^4$-[3-(4-{3-(isobutylamino)propyl}piperazino)propyl]-7-chloroquinolin-4-amine,
$N^4$-[3-(4-{3-(tert-pentylamino)propyl}piperazino)propyl]-7-chloroquinolin-4-amine,
$N^4$-[3-(4-{3-(cyclohexylmethylamino)propyl}piperazino) propyl]-7-chloroquinolin-4-amine,
$N^4$-(3-{4-[3-(diisobutylamino)propyl]piperizano}propyl)-benzimidazol-2-amine,
$N^4$-(3-{4-[3-(diisobutylamino)propyl]piperizano}propyl)-pyrimidin-2-amine,
$N^4$-(3-{4-[3-(diisobutylamino)propyl]piperizano}propyl)-pyrazin-2-amine,
$N^4$-(3-{4-[3-(diisobutylamino)propyl]piperizano}propyl)-purine-6-amine,
$N^4$-[3-{4-[3-(diisobutylamino)propyl]piperizano}propyl]-7-chloroquinolin-4-amine,
$N^4$-[3-(4-{3-[di(cyclopropylmethyl)amino] propyl}piperizano)propyl]-7-chloroquinolin-4-amine,
$N^4$-[3-(4-{3-[di(cyclopropylmethyl)amino] propyl}piperizano)propyl]-6-chloro-2-methoxyacridin-9-amine,
$N^4$-[3-(4-{3-[diisobutylamino]propyl}piperizano)propyl]-4-benzyloxyamine,
$N^4$-[3-(4-{3-[diisobutylamino]propyl}piperizano)propyl]-4-pyridinylmethylamine,
$N^4$-[3-(4-{3-[diisobutylamino]propyl}piperizano)propyl]-4-fluorobenzylamine,
$N^4$-[3-(4-{3-diisobutylamino]propyl}piperizano)propyl]-4-chlorobenzylamine,
$N^4$-[3-(4-{3-[diisobutylamino]propyl}piperizano)propyl]-2-thiazolylmethylamine,
$N^1$-[3-(4-3-[(7-chloro-4-quinolyl)amino]propylpiperizano) propyl]-$N^1$-cyclopropyl-methylcyclopropane-1-carboxamide,
Tert-butyl-N-3-[[3-(4-3-[(7-chloro-4-quinolyl)amino]propylpiperazino) propyl](cyclopropylmethyl)amino]-3-oxopropylcarbamate,
5-{[3-[3-(7-chloro-4-quinolyl)amino]propylpiperazino)propyl](cyclo propylmethyl)amino}pentanenitrile,
Tert-butyl-N-3-{[3-(4-[3-(7-chloro-4-quinolyl)amino]propylpiperazino) propyl](cyclopropylmethyl) amino}propylcarbamate,
1,4-bis(3-[diisobutylamino]propyl)piperazine, and
1,4-bis(3-[dicyclopropylmethylamino]propyl)piperazine.
1,4-bis{2-[4-chlorobenzyl)amino]ethyl}piperazine,
1,4-bis{2-[4-fluorobenzyl)amino]ethyl}piperazine,
1,4-bis{4-[4-chlorobenzyl)amino]butyl}piperazine,
1,4-bis{4-[4-fluorobenzyl)amino]butyl}piperazine,
N-(7-chloro-quinolin-4-yl)-N-3-[4-(3-pyrrolidin-1-yl-propyl)piperazin-1-yl]propylamine
N-(7-chloro-quinolin-4-yl)-N-3-[4-(3-piperidin-1-yl-propyl)piperazin-1-yl]propylamine
N-3-[4-(3-azepan-1-ylpropyl)piperazin-1-yl]propyl-N-(7-chloro-4-quinolyl)-amine
{3-[4-(3-Diisobutylamino-propyl)-piperazin-1-yl]-propyl}-(6-methyl-1H-benzimidazol-2-yl)-amine
{3-[4-(3-Diisobutylamino-propyl)-piperazin-1-yl]-propyl}-(6-methoxy-1H-benzimidazol-2-yl)-amine
(1H-Benzimidazol-2-yl)-{3-[4-(3-pyrrolidin-1-yl-propyl)-piperazin-1-yl]-propyl}-amine
(1H-Benzimidazol-2-yl)-{3-[4-(3-isobutylamino-propyl)-piperazin-1-yl]-propyl}-amine
1,4-bis{3-[N-(1H-Benzimidazol-2-yl)amino] propyl}piperazine
1,4-bis{3-[N-(anthr-9-ylmethyl)amino]propyl}piperazine
1,4-bis{3-[N-(Benzyl)amino]propyl}piperazine
1,4-bis{3-[N-(4-nitrobenzyl)amino]propyl}piperazine
1,4-bis{3-[N-(napht-2-ylmethyl)amino]propyl}piperazine
1,4-bis{3-[N-(4-phenylbenzyl)amino]propyl}piperazine
1,4-bis{3-[N-(3,4-dibenzyloxybenzyl)amino] propyl}piperazine
1,4-bis{3-[N-(fluoren-2-ylmethyl)amino]propyl}piperazine
1,4-bis{3-[N-(benzofur-2-ylmethyl)amino] propyl}piperazine
1,4-bis{3-[N-(quinol-2-ylmethyl)amino]propyl}piperazine Some compounds pertaining to anyone of said hereabove defined formula (Ia) to (Id) and (II) form part of the invention.

More specifically, the instant invention is also directed to the following compounds (1) to (21):
(1)
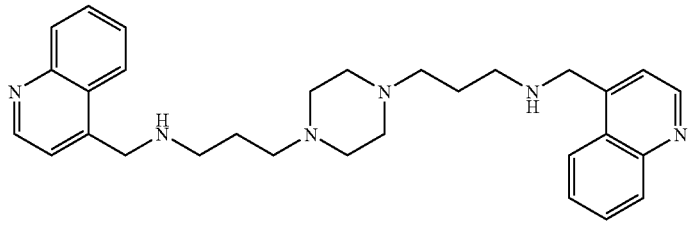
(2)
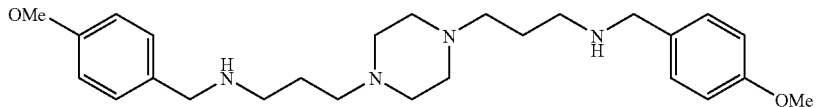
(3)
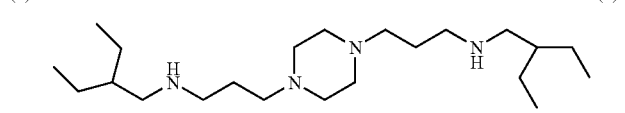
(4)
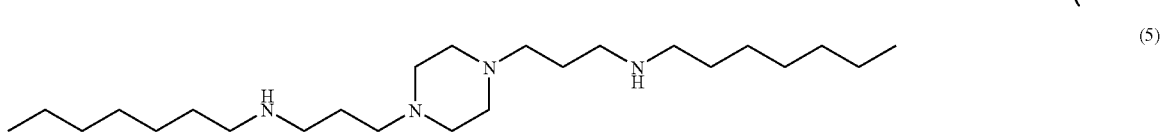
(5)
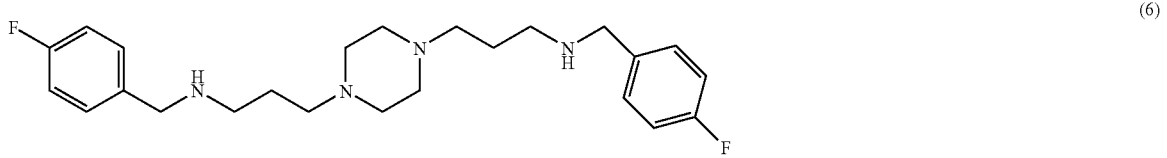
(6)
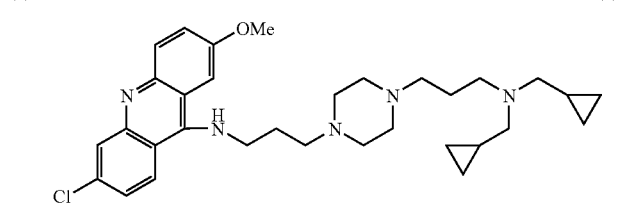
(7)
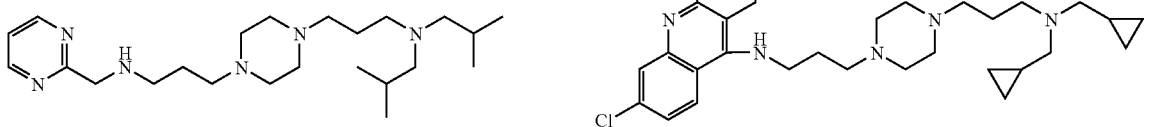
(8)
(9)
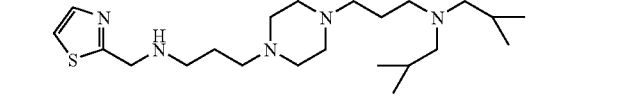
(10)
(11)
(12)
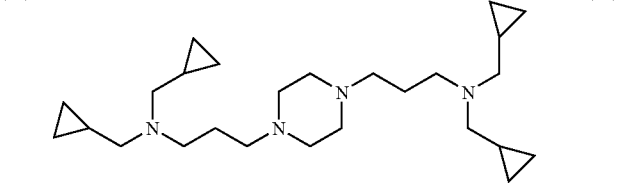

-continued
(13)
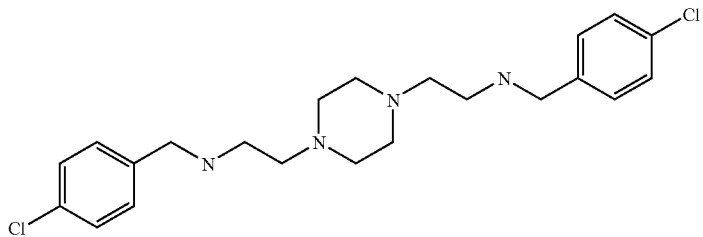
(14)
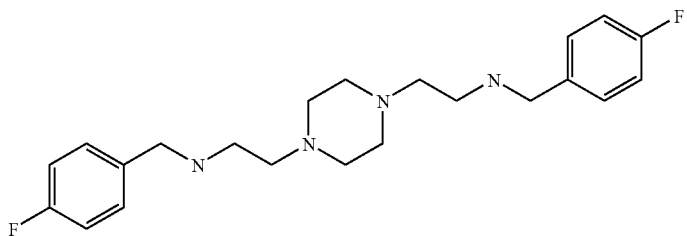
(15)
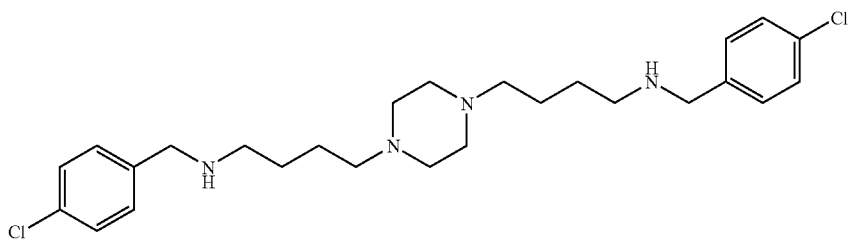
(16)
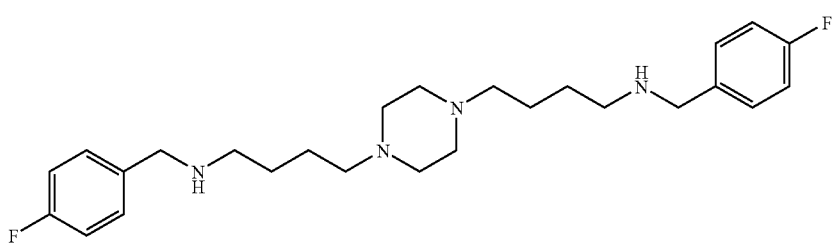
(17)
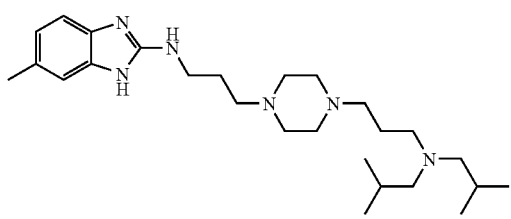
(18)
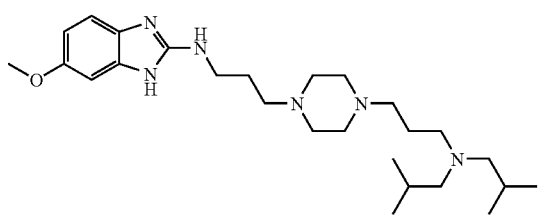
(19)
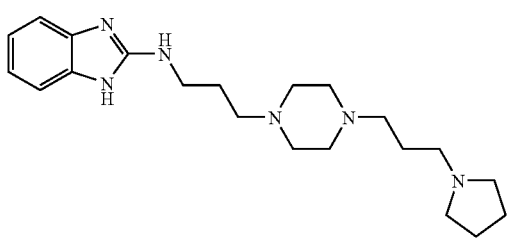
(20)
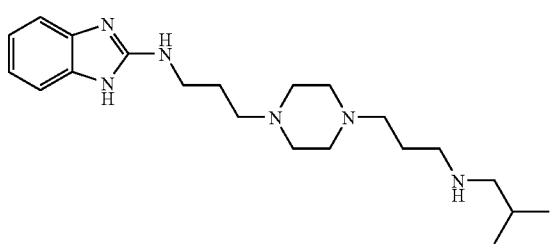

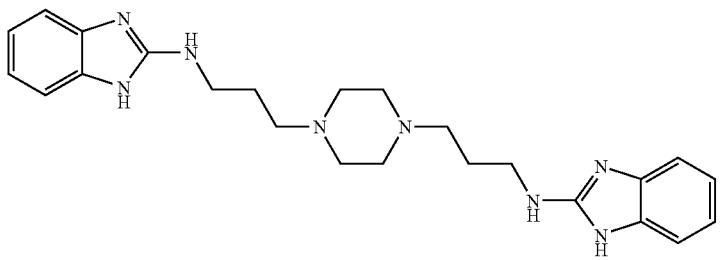

(21)

and their salts with pharmaceutically acceptable acids.

According to a further aspect of the invention, compounds of formula (II) hereinafter defined are also encompassed within the scope of the invention.

Therefore, the invention further relates to compounds of general formula (II)

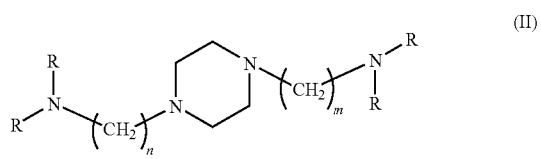

(II)

in which n and m are identical or different and independently represent an integer of greater than or equal to 2, particularly ranging from 2 to 8, more preferably ranging from 2 to 6, more particularly being 2, 3 or 4, the resulting hydrocarbon chain optionally comprising one or more heteroatoms selected among oxygen, nitrogen and sulphur, and, in which R is selected among a $(C_3-C_8)$alkyl group, straight or branched, saturated or unsaturated, an aralkyl group, an aryl group or, a heteroaryl group, where the group $(C_3-C_8)$alkyl can be possibly substituted by one or more identical or different groups chosen among a halogen, the cyano group, the hydroxy group, the nitro group, the amino group, a group $(C_1-C_7)$alkylamino, a group $(C_1-C_7)$alcoxy, a terbutoxycarbonylamino group, a HO—$(C_1-C_8)$alkyl-group, a $H_2N$—$(C_1-C_8)$alkyl-group, a HO—(C=O)— group, a $(C_1-C_9)$alkyl-O—(C=O)— group, a $(C_1-C_8)$alkyl-(C=O)— group, a $(C_1-C_8)$alkyl-(C=O)—$(C_1-C_8)$alkyl-group, a $HSO_3(C_1-C_8)$alkyl-group, a $H_2N$—(C=O)— group and a $H_2N$—(C=O)—$(C_1-C_8)$alkyl-group, where the aryl group is selected among the groups benzyl, phenyl, biphenyl, naphtyl, dihydronaphtyl, tetrahydronaphtyl, indenyl or indanyl, where the heteroaryl group is an aromatic monocycle, an aromatic bicycle, or a bicycle of which one of the cycles is aromatic and the other cycle is partially hydrogenated, from 5 to 12 links comprising within the cyclic system one, two or three heteroatoms, identical or different, selected among oxygen, nitrogen and sulphur and, where each one of these groups aryl or heteroaryl comprises possibly one or more substitutions, identical or different, chosen among a halogen, the hydroxy group, a $(C_1-C_7)$alkyl group, a $(C_1-C_7)$alcoxy group, the cyano group, the nitro group, the amino group, a $(C_1-C_7)$alkylamino group, a HO—$(C_1-C_9)$alkyl-group, a $H_2N$—$(C_1-C_8)$alkyl-group, a HO—(C=O)— group, a $(C_1-C_8)$alkyl-O—(C=O)— group, a $(C_1-C_8)$alkyl-(C=O)— group, a $(C_1-C_8)$alkyl-(C=O)—$(C_1-C_8)$alkyl-group, a $HSO_3(C_1-C_8)$alkyl-group, a $H_2N$—(C=O)— group and a $H_2N$—(C=O)—$(C_1-C_8)$alkyl-group, where ($R_1$ and $R_2$) and/or ($R_3$ and $R_4$), independently of one another, can possibly form an aromatic or partially hydrogenated $C_5$ to $C_{14}$ monocycle, optionally comprising within the cyclic system one, two or three heteroatoms, identical or different, selected among oxygen, nitrogen and sulphur, provided that compounds for which R represents a n-hexyl group or R represents a

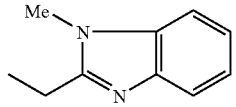

group are excluded, and their salts with pharmaceutically acceptable acids.

In one particular variant of the present invention the heteroaryl group is different from an acridin group or and acridin derivative. In another variant the heteroaryl group is different from an aromatic tricycle.

In the framework of the invention, n and m are possibly identical and more preferably equal to 2 or 3 or 4.

A "protective group" Pg means a group which makes it possible on the one hand to protect a reactive function such as a hydroxy or an amine during a synthesis and on the other hand to regenerate the intact reactive function at the end of the synthesis. Examples of protective groups as well as the methods of protection and deprotection are given in Protective groups in Organics Synthesis, Green and At, 2nd ED (John Wiley & Sons, Inc, New York).

A "leaving group" can easily be cleaved of a molecule by rupture of heteroliytic bindings, with departure of an electronic pair. This group can thus be replaced easily by, another group during a substitution reaction for example. Such groups therefore are, for example the halogens, or activated hydroxy groups such as a mesyl, tosyl, triflate, acetyl, etc. Examples of leaving groups as references related to said preparations are given in "Advances Organic Chemistry", J. March, 3rd Edition, Wiley Interscience, p 310-316.

The following schemes exemplify the preparation of compounds of formula (I) wherein n is equal to m and is equal to 3. Compounds of formula (I) wherein n and m are different from said definition may be prepared starting from the corresponding 1,4-bis(3-aminoalkyl)piperazine instead of compound of formula (V) as defined beneath.

The compounds of general formula (Ia) can be prepared according to scheme 1 below.

Scheme 1

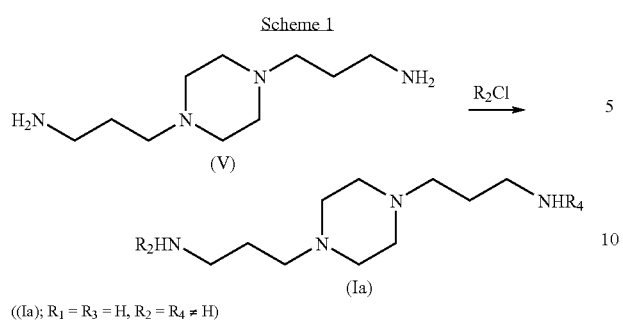

((Ia); R$_1$ = R$_3$ = H, R$_2$ = R$_4$ ≠ H)

According to this process, a derivative of formula (V), namely 1,4-bis(3-aminopropyl)piperazine can be reacted with a compound of formula R$_2$Cl, for example in the presence of K$_2$CO$_3$, for example in a solvent DMF, for example at a temperature ranging between 80 and 160° C., to obtain a compound of formula (Ia).

Other compounds of formula (Ia) can be obtained by reductive amination of a derivative of formula (V), namely 1,4-bis(3-aminopropyl)piperazine with an aldehyde of formula R$_2$'CHO, in the presence of sodium borohydride, in a solvent methanol, for example at a temperature ranging between 0 and 40° C., to obtain a compound of formula (Ia) (B. Bonnet et al, Bioorganic & Medicinal Chemistry 8 (2000) 95-103).

The compound of general formula (Ib) can be prepared according to scheme 2 below.

Scheme 2

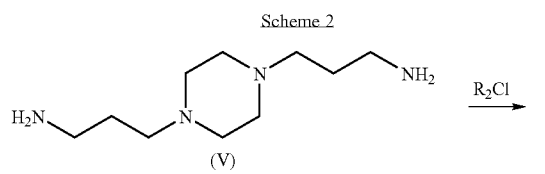

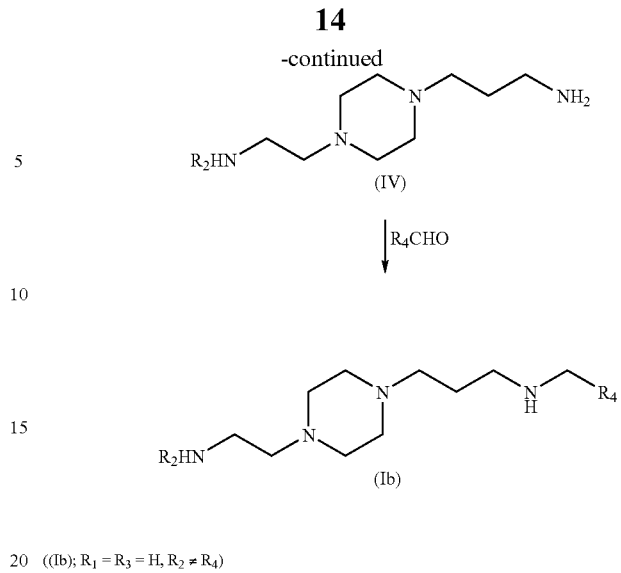

((Ib); R$_1$ = R$_3$ = H, R$_2$ ≠ R$_4$)

According to this process, a derivative of formula (V), namely 1,4-bis(3-aminopropyl)piperazine is reacted with a compound of formula R$_2$Cl, for example in a solvent pentanol, for example at a temperature ranging between 80° and 160° C., to obtain the compound of formula (IV). Compounds of formula (Ib) are obtained by reductive amination of a derivative of formula (I), with an aldehyde of formula R$_4$—CHO, in the presence of sodium borohydride, in a solvent methanol, for example at a temperature ranging between 0 and 40° C., to obtain a compound of formula (Ib) (A. Ryckebusch et al, J. Med. Chem. (2003), 46, 542-557).

The compound of general formula (Ic) can be prepared according to scheme 3 below.

Scheme 3

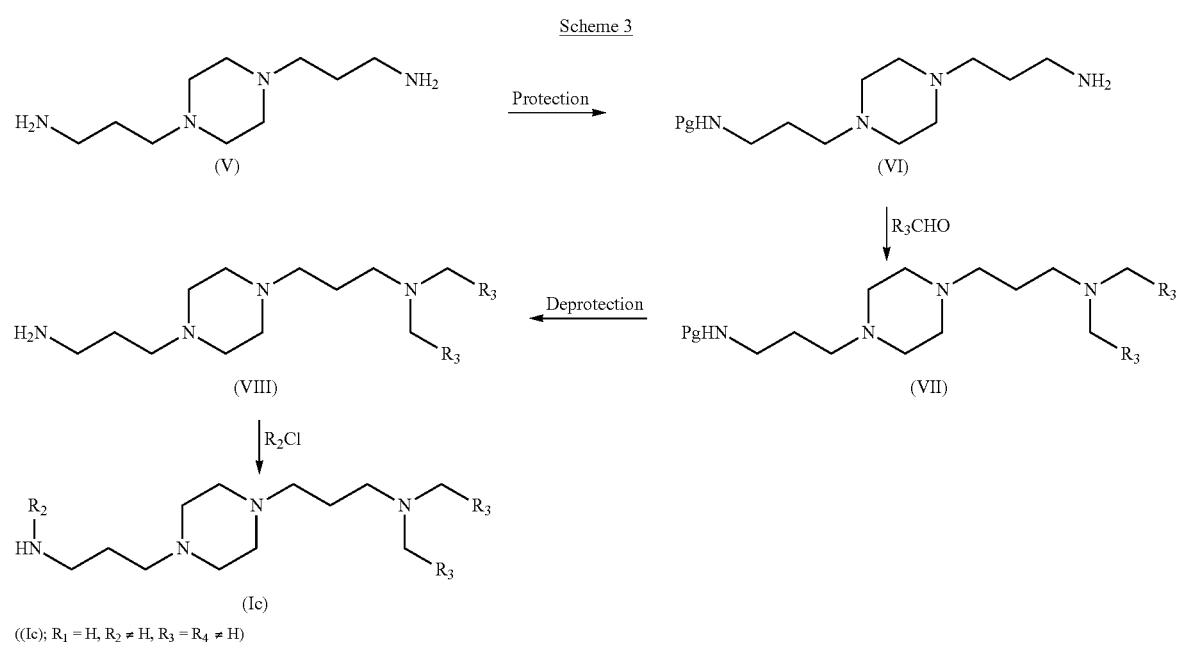

((Ic); R$_1$ = H, R$_2$ ≠ H, R$_3$ = R$_4$ ≠ H)

According to this process, a derivative of formula (V), namely 1,4-bis(3-aminopropyl)piperazine can be reacted with di-tert-dicarbonate, for example in the presence of sodium hydroxyde, for example in a solvent dioxane, for example at a temperature ranging between 0° and 25° C., to obtain the compound of formula (VI). Compounds of formula (VII) can be obtained by reductive amination of a derivative of formula (VI), with an aldehyde of formula $R_3CHO$, in the presence of sodium acetoxyborohydride, in a solvent methylene chloride, for example at a temperature ranging between 0 and 40° C. Compounds of formula (VIII) can be obtained by deprotection of a derivative of formula (VII), with an trifluoroacetic acid, in a solvent methylene chloride, for example at a temperature ranging between 0 and 40° C. Compounds of formula (Ic) can be obtained by reaction of a compound of formula $R_2Cl$, with compound of formula (VIII), in a solvent pentanol, for example at a temperature ranging between 80° and 160° C., to obtain a compound of formula (Ic).

The compound of general formula (Id) can be prepared according to scheme 4 below.

Scheme 4

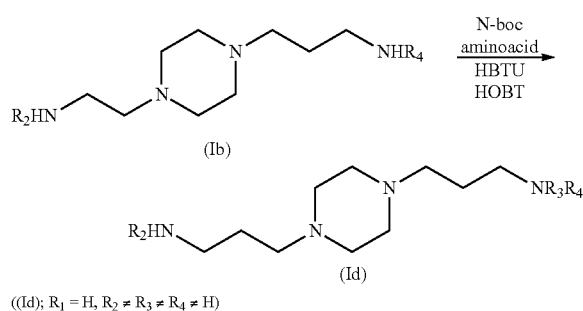

((Id); $R_1 = H, R_2 \neq R_3 \neq R_4 \neq H$)

In the scheme HOBT refers to hydroxybenzotriazole and HBTU refers to 2-(1H-benzotriazole-1-yl)-1,1,3,3-tetramethyluronium hexafluorophosphate.

According to this process, a derivative of formula (Ib), can be reacted with N-Boc-aminoacid, for example in the presence of HOBT, HBTU and N,N-diisopropylethylamine, for example in a solvent methylene chloride, for example at a temperature ranging between 0° and 40° C., to obtain a compound of formula (Id).

The compound of general formula (II) can be prepared according to scheme 5 below.

Scheme 5

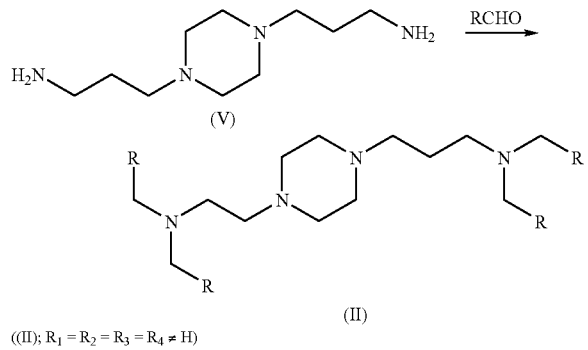

((II); $R_1 = R_2 = R_3 = R_4 \neq H$)

According to this process, a derivative of formula (V), namely 1,4-bis(3-aminopropyl)piperazine can be reacted with an aldehyde of formula RCHO, for example in the presence of sodium acetoxyborohydride, for example in a solvent methylene chloride, for example at a temperature ranging between 0° and 40° C., to obtain a compound of formula (II).

The starting compounds are commercially available or can be prepared according to methods known to the person skilled in the art.

For example, the compound of formula (V) is commercially available.

The corresponding starting compounds of formula (IX)

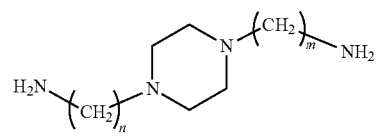

where n and m are different from 3, are not commercially available.

Synthesis of said starting compound of formula (IX) where n and m are simultaneously equal to 2 may be performed by anyone of the two chemical routes summarized hereinafter in schemes 6 and 7:

Scheme 6

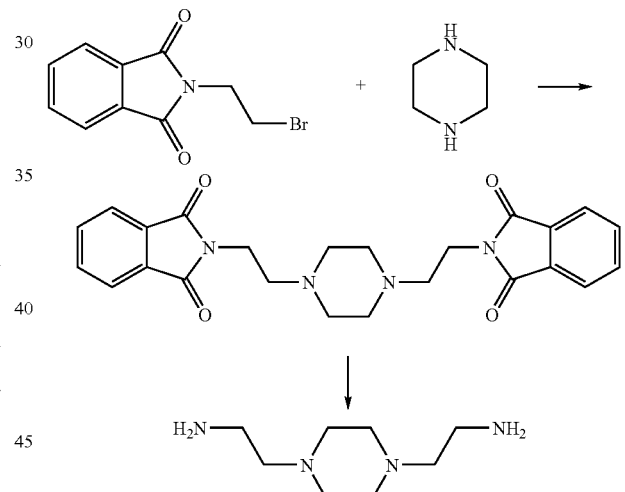

(Von Braun, Goll, Metz *Chem.Ber.* 1926, 59, 2423-Kermack, Smith *J. Chem. Soc.* 1931, 3096-Ganin et al. *J. Org. Chem. USSR* (Engl.Transl.) 1987, 23, 330)

Scheme 7

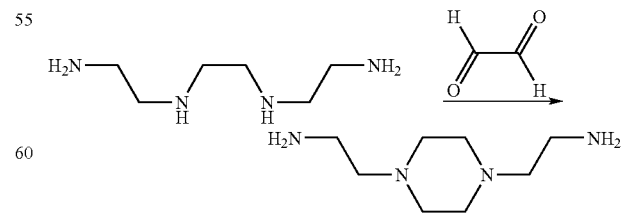

(Chuburu et al. *Eur. J. Org. Chem.* 2003, 6, 1050)

The starting compound of formula (IX) where n and m are simultaneously equal to 4 may be prepared according to the following scheme 8:

Scheme 8

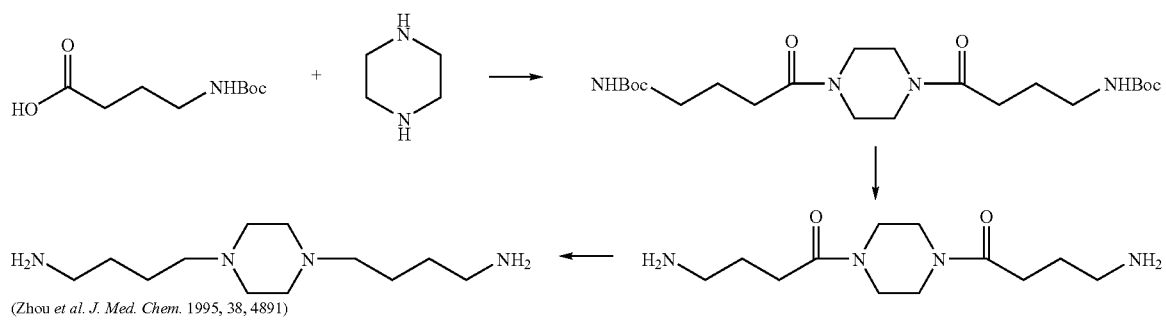

(Zhou et al. J. Med. Chem. 1995, 38, 4891)

The synthesis of compounds of formula (IX) where n and m are different may be carried out by solid-phase synthesis, for example by the method described in J. Renault et al. Tetrahedron Letters 42 (2001) 6655-6658.

The following Examples illustrate in detail the preparation of some compounds according to the invention, and more particularly compounds chosen among compounds (1) to (13) and of formula (II). The structures of the products obtained have been confirmed by NMR spectra.

EXAMPLE 1

1,4-bis{3-[N-(7-chloroquinolin-4-yl)amino]propyl}piperazine

A solution of 4,7-dichloroquinoline (1.58 g, 8.0 mmol) and 1,4-bis(3-aminopropyl)piperazine (0.33 mL, 1.6 mmol) in DMF (5 mL) is refluxed (160° C.) for 18 h in the presence of $K_2CO_3$ (1.77 g, 12.8 mmol). After evaporation, the media is diluted with HCl 1M, and washed with ethyl acetate. Aqueous layer is alcalinised with $NaHCO_3$, extracted with $CH_2Cl_2$, and dried over $MgSO_4$. Crude compound is purified by precipitation in ethyl acetate.

m/z (MALDI)=523.2

EXAMPLE 2

1,4-bis{3-[N-(pyrid-3-ylmethyl)amino]propyl}piperazine

To a solution of 1,4-bis(3-aminopropyl)piperazine (0.51 mL, 2.5 mmol) and 3-pyridinecarboxaldehyde (561 mg, 5.24 mmol) in absolute ethanol (20 mL), 3 Å molecular sieves are added. After stirring the mixture at room temperature for 12 h, $NaBH_4$ (1.9 g, 249.92 mmol) was added portionwise and the mixture was stirred for 12 h at room temperature. The reaction was quentched by dropwise addition of water (20 mL) and ethanol was removed under reduced pressure. The aqueous residue was extracted with $CH_2Cl_2$ (3×30 mL). Combined organic layers were extracted with HCl 1M. The combined aqueous layers were neutralized with NaOH 1M and extracted with $CH_2Cl_2$. Combined organic layers were dried over $MgSO_4$. Crude compound is purified by flash chromatography on neutral aluminium oxide ($CH_2Cl_2$/MeOH).

m/Z (MALDI)=383.3

EXAMPLE 3

1,4-bis{3-[N-(3,4-dimethoxybenzyl)amino]propyl}piperazine

To a solution of 1,4-bis(3-aminopropyl)piperazine (0.51 mL, 2.5 mmol) and 3,4-dimethoxybenzaldehyde (871 mg, 5.24 mmol) in absolute ethanol (20 mL), 3 Å molecular sieves are added. After stirring the mixture at room temperature for 12 h, $NaBH_4$ (1.9 g, 49.92 mmol) was added portionwise and the mixture was stirred for 12 h at room temperature. The reaction was quentched by dropwise addition of water (20 mL) and ethanol was removed under reduced pressure. The aqueous residue was extracted with $CH_2Cl_2$ (3×30 mL). Combined organic layers were extracted with HCl 1M. The combined aqueous layers were neutralized with NaOH 1M and extracted with $CH_2Cl_2$. Combined organic layers were dried over $MgSO_4$. Crude compound is purified by flash chromatography on neutral aluminium oxide ($CH_2Cl_2$/MeOH).

m/z (MALDI)=501.4

EXAMPLE 4

1,4-bis{3-[4-chlorobenzyl)amino]propyl}piperazine

To a solution of 1,4-bis(3-aminopropyl)piperazine (0.51 mL, 2.5 mmol) and 4-chlorobenzaldehyde (737 mg, 5.24 mmol) in absolute ethanol (20 mL), 3 Å molecular sieves are added. After stirring the mixture at room temperature for 12 h, $NaBH_4$ (1.9 g, 49.92 mmol) was added portionwise and the mixture was stirred for 12 h at room temperature. The reaction was quentched by dropwise addition of water (20 mL) and ethanol was removed under reduced pressure. The aqueous residue was extracted with $CH_2Cl_2$ (3×30 mL). Combined organic layers were extracted with HCl 1M. The combined aqueous layers were neutralized with NaOH 1M and extracted with $CH_2Cl_2$. Combined organic layers were dried over $MgSO_4$. Crude compound is purified by flash chromatography on neutral aluminium oxide ($CH_2Cl_2$/MeOH).

m/z (MALDI)=449.3

EXAMPLE 5

Compound No. 1

1,4-bis{3-[N-(quinol-4-ylmethyl)amino]propyl}piperazine

To a solution of 1,4-bis(3-aminopropyl)piperazine (0.51 mL, 2.5 mmol) and 4-quinolinecarboxaldehyde (824 mg, 5.24 mmol) in absolute ethanol (20 mL), 3 Å molecular sieves are added. After stirring the mixture at room temperature for 12 h, $NaBH_4$ (1.9 g, 249.92 mmol) was added portionwise and the mixture was stirred for 12 h at room temperature. The reaction was quentched by dropwise addition of water (20 mL) and ethanol was removed under reduced pressure. The aqueous residue was extracted with $CH_2Cl_2$ (3×30 mL). Combined organic layers were extracted with HCl 1M. The combined aqueous layers were neutralized with NaOH 1M and extracted with $CH_2Cl_2$. Combined organic layers were dried over $MgSO_4$. Crude compound is purified by flash chromatography on neutral aluminium oxide ($CH_2Cl_2$/MeOH).

m/z (MALDI)=483.4

EXAMPLE 6

Compound No. 2

1,4-bis{3-[N-(4-methoxybenzyl)amino]propyl}piperazine

To a solution of 1,4-bis(3-aminopropyl)piperazine (0.51 mL, 2.5 mmol) and p-anisaldehyde (636 µL, 5.24 mmol) in absolute ethanol (20 mL), 3 Å molecular sieves are added. After stirring the mixture at room temperature for 12 h, $NaBH_4$ (1.9 g, 49.92 mmol) was added portionwise and the mixture was stirred for 12 h at room temperature. The reaction was quenched by dropwise addition of water (20 mL) and ethanol was removed under reduced pressure. The aqueous residue was extracted with $CH_2Cl_2$ (3×30 mL). Combined organic layers were extracted with HCl 1M. The combined aqueous layers were neutralized with NaOH 1M and extracted with $CH_2Cl_2$. Combined organic layers were dried over $MgSO_4$. Crude compound is purified by flash chromatography on neutral aluminium oxide ($CH_2Cl_2$/MeOH).

m/z (MALDI)=441.3

EXAMPLE 7

1,4-bis{3-[N-(cyclopropylmethyl)amino]propyl}piperazine

To a solution of 1,4-bis(3-aminopropyl)piperazine (0.51 mL, 2.5 mmol) and cyclopropanecarboxaldehyde (6392 µL, 5.24 mmol) in absolute ethanol (20 mL), 3 Å molecular sieves are added. After stirring the mixture at room temperature for 12 h, $NaBH_4$ (1.9 g, 49.92 mmol) was added portionwise and the mixture was stirred for 12 h at room temperature. The reaction was quenched by dropwise addition of water (20 mL) and ethanol was removed under reduced pressure. The aqueous residue was extracted with $CH_2Cl_2$ (3×30 mL). Combined organic layers were extracted with HCl 1M. The combined aqueous layers were neutralized with NaOH 1M and extracted with $CH_2Cl_2$. Combined organic layers were dried over $MgSO_4$. Crude compound is purified by flash chromatography on neutral aluminium oxide ($CH_2Cl_2$/MeOH).

m/z (MALDI)=309.3

EXAMPLE 8

Compound No. 3

1,4-bis{3-[N-(isobutyl)amino]propyl}piperazine

To a solution of 1,4-bis(3-aminopropyl)piperazine (0.51 mL, 2.5 mmol) and isobutylaldehyde (476 µL, 5.24 mmol) in absolute ethanol (20 mL), 3 Å molecular sieves are added. After stirring the mixture at room temperature for 12 h, NaBH (1.9 g, 49.92 mmol) was added portionwise and the mixture was stirred for 12 h at room temperature. The reaction was quenched by dropwise addition of water (20 mL) and ethanol was removed under reduced pressure. The aqueous residue was extracted with $CH_2Cl_2$ (3×30 mL). Combined organic layers were extracted with HCl 1M. The combined aqueous layers were neutralized with NaOH 1M and extracted with $CH_2Cl_2$. Combined organic layers were dried over $MgSO_4$. Crude compound is purified by flash chromatography on neutral aluminium oxide ($CH_2Cl_2$/MeOH).

m/z (MALDI)=313.3

EXAMPLE 9

Compound No. 4

1,4-bis{3-[N-(2-ethylbutyl)amino]propyl}piperazine

To a solution of 1,4-bis(3-aminopropyl)piperazine (0.51 mL, 2.5 mmol) and 2-ethylbutyraldehyde (645 µL, 5.24 mmol) in absolute ethanol (20 mL), 3 Å molecular sieves are added. After stirring the mixture at room temperature for 12 h, $NaBH_4$ (1.9 g, 49.92 mmol) was added portionwise and the mixture was stirred for 12 h at room temperature. The reaction was quenched by dropwise addition of water (20 mL) and ethanol was removed under reduced pressure. The aqueous residue was extracted with $CH_2Cl_2$ (3×30 mL). Combined organic layers were extracted with HCl 1M. The combined aqueous layers were neutralized with NaOH 1M and extracted with $CH_2Cl_2$. Combined organic layers were dried over $MgSO_4$. Crude compound is purified by flash chromatography on neutral aluminium oxide ($CH_2Cl_2$/MeOH).

m/z (MALDI)=369.4

EXAMPLE 10

Compound No. 5

1,4-bis{3-[N-n-heptyl)amino]propyl}piperazine

To a solution of 1,4-bis(3-aminopropyl)piperazine (0.51 mL, 2.5 mmol) and heptanal (732 µL, 5.24 mmol) in absolute ethanol (20 mL), 3 Å molecular sieves are added. After stirring the mixture at room temperature for 12 h, $NaBH_4$ (1.9 g, 49.92 mmol) was added portionwise and the mixture was stirred for 12 h at room temperature. The reaction was quenched by dropwise addition of water (20 mL) and ethanol was removed under reduced pressure. The aqueous residue was extracted with $CH_2CH_2$ (3×30 mL). Combined organic layers were extracted with HCl 1M. The combined aqueous layers were neutralized with NaOH 1M and extracted with $CH_2Cl_2$. Combined organic layers were dried over $MgSO_4$. Crude compound is purified by flash chromatography on neutral aluminium oxide ($CH_2Cl_2$/MeOH).

m/z (MALDI)=397.4

EXAMPLE 11

Compound No. 6

1,4-bis{3-[N-(4-fluorobenzyl)amino]propyl}piperazine

To a solution of 1,4-bis(3-aminopropyl)piperazine (0.51 mL, 2.5 mmol) and 4-fluorobenzaldehyde (0.59 mL, 5.5 mmol) in absolute ethanol (20 mL), 3 Å molecular sieves are added. After stirring the mixture at room temperature for 5 h, NaBH (0.47 g, 12.5 mmol) was added portionwise and the mixture was stirred for 12 h at room temperature. The reaction was quentched by dropwise addition of water (20 mL) and ethanol was removed under reduced pressure. The aqueous residue was extracted with CH$_2$Cl$_2$ (3×30 mL). Combined organic layers were extracted with HCl 1M. The combined aqueous layers were neutralized with NaOH 1M and extracted with CH$_2$Cl$_2$. Combined organic layers were dried over MgSO$_4$. Crude compound is purified thick-layer chromatography (acetone/NH$_4$OH:90/10).

m/z (MALDI)=417.3

EXAMPLE 12

N$^4$-[3-(4-{3-[(cyclopropylmethyl)amino]propyl}piperazino)propyl]-7-chloroquinolin-4-amine a) N$^4$-3-[4 (3-aminopropyl)piperazine]propyl-7-chloroquinolin-4-amine (Intermediate)

A solution of 4,7-dichloroquinoline (1.0 g, 5.05 mmol) and 1,4-bis(3-aminopropyl)piperazine (3.1 mL, 15.1 mmol) in 1-pentanol (5.5 mL) is refluxed (160° C.) for 18 h. After cooling, the media is diluted with 50 mL CH$_2$Cl$_2$ washed with NaOH 10% (3×50 mL), dried over MgSO$_4$. Crude compound is purified by flash chromatography (CH$_2$Cl$_2$/MeOH/NH$_4$OH:80/20/0.9).

m/z (MALDI)=360.5 b) N$^4$-[3-(4-{3-[(cyclopropylmethyl)amino]propyl}piperazino)propyl]-7-chloroquinolin-4-amine To a solution of the compound obtain in the preceeding step (150 mg, 0.41 mmol) in CH$_2$Cl$_2$ (4 mL) cyclopropane-1-carboxaldehyde (51 µL, 0.46 mmol), triethylamine (26 µL, 0.16 mmol) and 3 Å molecular sieves are added. The reaction media is stirred for 3 h and cooled before NaBH$_4$ (78 mg, 2.05 mmol) is added portionwise over 30 min. Stirring is left for 1.5 h, water (10 mL) is added and the media is filtered. Compound is extracted with CH$_2$Cl$_2$ (3×20 mL). Combined organic layers are dried over MgSO$_4$. Crude compound is purified by thick-layer chromatography (CH$_2$Cl$_2$/MeOH/NH$_4$OH: 80/20/1.8).

m/z (TOF)=416.2

EXAMPLE 13

N$^4$-[3-(4-{3-(isobutylamino)propyl}piperazino)propyl]-7-chloroquinolin-4-amine To a solution of N$^4$-3-[4(3-aminopropyl)piperazine]propyl-7-chloroquinolin-4-amine (Intermediate of example 12) (150 mg, 0.41 mmol) in CH$_2$C$_2$ (4 mL) isobutyraldehyde (62 µL, 0.46 mmol), triethylamine (26 µL, 0.16 mmol) and 3 Å molecular sieves are added. The reaction media is stirred for 3 h and cooled before NaBH$_4$ (78 mg, 2.05 mmol) is added portionwise over 30 min. Stirring is left for 1.5 h, water (10 mL) is added and the media is filtered. Compound is extracted with CH$_2$Cl$_2$ (3×20 mL). Combined organic layers are dried over MgSO$_4$. Crude compound is purified by thick-layer chromatography (CH$_2$Cl$_2$/MeOH/NH$_4$OH:90/10/1.4).

m/z (TOF)=418.3

EXAMPLE 14

N$^4$-[3-(4-{3-(tert-pentylamino)propyl}piperazino)propyl]-7-chloroquinolin-4-amine To a solution of N$^4$-3-[4(3-aminopropyl)piperazine]propyl-7-chloroquinolin-4-amine (Intermediate of example 12) (150 mg, 0.41 mmol) in CH$_2$Cl$_2$ (4 mL) trimethylacetaldehyde (40 mg, 0.46 mmol), triethylamine (26 µL, 0.16 mmol) and 3 Å molecular sieves are added. The reaction media is stirred for 3 h and cooled before NaBH$_4$ (78 mg, 2.05 mmol) is added portionwise over 30 min. Stirring is left for 1.5 h, water (10 mL) is added and the media is filtered. Compound is extracted with CH$_2$Cl$_2$ (3×20 mL). Combined organic layers are dried over MgSO$_4$. Crude compound is purified by thick-layer chromatography (CH$_2$Cl$_2$/MeOH/NH$_4$OH:90/10/1).

m/z (TOF)=432.4

EXAMPLE 15

N$^4$-[3-(4-{3-(cyclohexylmethylamino)propyl}piperazino)propyl]-7-chloroquinolin-4-amine To a solution of N$^4$-3-[4(3-aminopropyl)piperazine]propyl-7-chloroquinolin-4-amine (Intermediate of example 12) (150 mg, 0.41 mmol) in CH$_2$Cl$_2$ (4 mL) cyclohexane-1-carboxaldehyde (83 µL, 0.46 mmol), triethylamine (26 µL, 0.16 mmol) and 3 Å molecular sieves are added. The reaction media is stirred for 3 h and cooled before NaBH$_4$ (78 mg, 2.05 mmol) is added portionwise over 30 min. Stirring is left for 1.5 h, water (10 mL) is added and the media is filtered. Compound is extracted with CH$_2$Cl$_2$ (3×20 mL). Combined organic layers are dried over MgSO$_4$. Crude compound is purified by thick-layer chromatography (CH$_2$Cl$_2$/MeOH/NH$_4$OH:90/10/1.4).

m/z (TOF)=458.4

EXAMPLE 16

N$^4$-(3-{4-[3(diisobutylamino)propyl]piperizano}propyl)-benzimidazol-2-amine a) N$^4$-(3-{4-[3-(diisobutylamino)propyl]piperizano}propyl)-amine (Intermediate Synthesised in 3 Steps)

Step 1: Synthesis of N-(3-{4-[3-(tert-butylcarbobenzyloxyamino)propyl]piperizano}propyl)amine To a solution of 1,4-bis(3-aminopropyl)piperazine (5.0 g, 24.9 mmol) in dry dioxane (25 mL) NaOH 0.5M (60 mL) then Boc$_2$O (150 mg, 0.41 mmol) in dry dioxane (25 mL) are added dropwise. The reaction media is stirred for 48 h, evaporated and solubilized in CH$_2$Cl$_2$. NaOH 1M is added. Organic layer is separated and aqueous layer is washed with CH$_2$Cl$_2$. Combined organic layers are dried over MgSO$_4$. Crude compound is purified by thick-layer chromatography (CH$_2$Cl$_2$/MeOH/NH$_4$OH: 80/20/0.9).

m/z (MALDI)=301.3

Step 2: Synthesis of N,N-diisobutyl-N-(3-{4[3-(tert-butylcarbobenzyloxyamino) propyl]piperizano}propyl)amine To a solution of N-(3-{4-[3-(tert-butylcarbobenzyloxyamino)propyl]piperizano}propyl)amine (2.86 g, 9.52 mmol) in dry CH$_2$Cl$_2$ (25 mL) isobutyraldehyde (2.6 mL, 28.6 mmol) and NaHB(OAc)$_3$ (6.05 g, 28.6 mmol) in dry CH$_2$Cl$_2$ (25 mL) are added dropwise. The reaction media is stirred for 18 h and NaOH 1M (5 mL) is added. Organic layer is separated and aqueous layer is washed with CH$_2$Cl$_2$. Combined organic layers are dried over MgSO$_4$. Crude compound is purified by thick-layer chromatography (CH$_2$Cl$_2$/MeOH/NH$_4$OH: 90/10/0.9).
m/z (MALDI)=413.3

Step 3: Synthesis of the Intermediate

A solution of N,N-diisobutyl-N-(3-{4-[3-(tert-butylcarbobenzyloxyamino) propyl]piperizano}propyl)amine (0.701 g, 1.70 mmol) in TFA/CH$_2$Cl$_2$: 1/1 (20 mL) is stirred overnight. After evaporation triethylamine is added until neutralisation. After evaporation to dryness, the residue is solubilized in CH$_2$Cl$_2$, washed with NaOH 2.5M and dried over MgSO$_4$.
m/z (MALDI)=313.2 b) 1-{3-[4-(3-Diisobutylamino-propyl)-piperazin-1-yl]-propyl}-3-(2-nitro-phenyl)-thiourea To a solution of N$^4$-(3-{4-[3-(diisobutylamino)propyl]piperizano}propyl)-amine (372 mg, 1.19 mmol) in THF (10 mL), 2-nitrophenyl isothiocyanate (244 mg, 1.31 mmol) was added portionwise and the reaction media has been stirred for 24 h at room temperature. After evaporation, crude compound is purified by flash chromatography (CH$_2$Cl$_2$/MeOH: 90/10).
m/z (MALDI)=493.5 c) {3-[4-(3-Diisobutylamino-propyl)-piperazin-1-yl]-propyl}-(1H-benzimidazol-2-yl)-amine To a solution of thiourea (282 mg, 0.57 mmol) in absolute ethanol (13 mL), SnCl$_2$ (217 mg, 1.14 mmol) is added. After stirring the mixture at reflux for 24 h, the solvent was removed under reduced pressure. NaOH 1M (20 mL) was added and the aqueous layer was extracted several times with CH$_2$Cl$_2$. Combined organic layers were washed with brine and dried over MgSO$_4$. Crude compound is purified by flash chromatography (CH$_2$Cl$_2$/MeOH/NH$_4$OH: 90/10/0.2).
m/z (MALDI)=429.3
Compound is used as its oxalate salt

EXAMPLE 17

Compound No. 7

N$^4$-(3-{4-[3-(diisobutylamino)propyl]piperizano}propyl)-pyrimidin-2-amine

A solution of intermediate of Example 16 (175 mg, 0.56 mmol), triethylamine (0.39 mL, 2.80 mmol) and 2-chloropyrimidin (193 mg, 1.68 mmol) in 2-pentanol (3 .mL) is refluxed for 48 h. After cooling to room temperature, the medium is diluted with CH$_2$Cl$_2$ (40 mL), organic layer washed with NaOH 2.5M and dried over MgSO$_4$. Crude compound is purified by thick-layer chromatography (CH$_2$Cl$_2$/MeOH/NH$_4$OH: 90/10/0.9).
m/z (MALDI)=391.30

EXAMPLE 18

N$^4$-(3-{4-[3-(diisobutylamino)propyl]piperizano}propyl)-pyrazin-2-amine

A solution of intermediate of Example 16 (190 mg, 0.61 mmol), triethylamine (0.43 mL, 3.04 mmol) and 2-chloropyrazine (0.163 mL, 1.83 mmol) in 2-pentanol (4 .mL) is refluxed for 48 h. After cooling to room temperature, the medium is diluted with CH$_2$Cl$_2$ (40 mL), organic layer washed with NaOH 2.5M and dried over MgSO$_4$. Crude compound is purified by thick-layer chromatography (CH$_2$Cl$_2$/MeOH/NH$_4$OH: 90/10/1.8).
m/z (MALDI)=391.25

EXAMPLE 19

N$^4$-(3-{4-[3-(diisobutylamino)propyl]piperizano}propyl)-purine-6-amine

A solution of intermediate of Example 16 (220 mg, 0.71 mmol), triethylamine (0.49 mL, 3.52 mmol), diisopropylethylamine (0.123 mL, 0.705 mmol) and 6-chloropurine (327 mg, 2.11 mmol) in 2-pentanol (4 mL) is refluxed for 3 h. After cooling to room temperature, the medium is diluted with CH$_2$Cl$_2$ (40 mL), organic layer washed with, NaOH 2.5M and dried over MgSO$_4$. Crude compound is purified by thick-layer chromatography (CH$_2$Cl$_2$/MeOH/NH$_4$OH: 90/10/0.9).
m/z (MALDI)=431.25

EXAMPLE 20

N$^4$-[3-{4-[3-(diisobutylamino)propyl]piperizano}propyl)-7-chloroquinoin-4-amine To a solution of N$^4$-3-[4(3-aminopropyl)piperazine]propyl-7-chloroquinolin-4-amine (Intermediate of example 12) (150 mg, 0.41 mmol) in dry CH$_2$Cl$_2$ (1.5 mL) isobutyraldehyde (169 µL, 1.24 mmol) and NaHB(OAc)$_3$ (263 mg, 1.23 mmol) in dry CH$_2$Cl$_2$ (1.5 mL) are added dropwise. The reaction media is stirred for 4 h and NaOH 1M (5 mL) is added. Organic layer is separated and aqueous layer is washed with CH$_2$Cl$_2$. Combined organic layers are dried over MgSO$_4$. Crude compound is purified by thick-layer chromatography (CH$_2$Cl$_2$/MeOH/NH$_4$OH: 90/10/0.9).
m/z (MALDI)=474.2

EXAMPLE 21

N$^4$-[3-(4-{3-[di(cyclopropylmethyl)amino]propyl}piperizano)propyl]-7-chloroquinolin-4-amine To a solution of N$^4$-3-[4(3-aminopropyl)piperazine]propyl-7-chloroquinolin-4-amine (Intermediate of example 12) (150 mg, 0.41 mmol) in dry CH$_2$Cl$_2$ (3 mL) cyclopropane-1-carboxaldehyde (139 mL, 1.24 mmol) and NaHB(OAc)$_3$ (263 mg, 1.23 mmol) are added. The reaction media is stirred for 4 h and NaOH 1M (5 mL) is added. Organic layer is separated and aqueous layer is washed with CH$_2$Cl$_2$. Combined organic layers are dried over MgSO$_4$. Crude compound is purified by thick-layer chromatography (CH$_2$Cl$_2$/MeOH/NH$_4$OH: 90/10/0.9).
m/z (MALDI)=470.4

EXAMPLE 22

Compound No. 8

N$^4$-[3-(4-{3-[di(cyclopropylmethyl)amino]propyl}piperizano)propyl]-6-chloro-2-methoxyacridin-9-amine a) N'-3-[4-(3-aminopropyl)piperazine]propyl-6-chloro-2-methoxyacridin-9-amine (Intermediate)

A solution of 6,9-dichloro-2-methoxyacridin (1.0 g, 3.6 mmol) and 1,4-bis(3-aminopropyl)piperazine (2.2 mL, 10.8 mmol) in 1-pentanol (18 mL) is refluxed (160° C.) for 4 h. After cooling, the media is diluted with 50 mL CH$_2$Cl$_2$, washed with NaOH 10% (3×50 mL), dried over MgSO$_4$. Crude compound is purified by flash chromatography (CH$_2$Cl$_2$/MeOH/NH$_4$OH: 80/20/0.9).

b) N$^4$-[3-(4-{3-[di(cyclopropylmethyl)amino] propyl}piperizano)propyl]-6-chloro-2-methoxyacridin-9-amine To a solution of the intermediate obtained in the preceding step (238 mg, 0.54 mmol) in dry CH$_2$Cl$_2$ (1.5 mL) cyclopropane-1-carboxaldehyde (160 µL, 2.15 mmol) and NaHB(OAc)$_3$ (456 mg, 2.15 mmol) are added. The reaction media is stirred for 4 h and NaOH 1M (5 mL) is added. Organic layer is separated and aqueous layer is washed with CH$_2$Cl$_2$. Combined organic layers are dried over MgSO$_4$. Crude compound is purified by thick-layer chromatography (CH$_2$Cl$_2$/MeOH/NH$_4$OH: 90/10/0.9).
m/z (MALDI)=550.16

EXAMPLE 23

N$^4$-[3-(4-{3-[diisobutylamino]propyl}piperizano)propyl]-4-benzyloxyamine

To a solution of the intermediate obtained in example 16 (150 mg, 0.48 mmol) in dry methanol (3 mL) para-anisaldehyde (64 µL, 0.53 mmol), triethylamine (27 µL, 0.19 mmol) and 3 Å molecular sieves are added. The reaction media is stirred for 3 h, cooled to 0° C. NaBH$_4$ (109 mg, 2.89 mmol) is added portionwise for 30 min. After 1.5 h stirring, the reaction is hydrolysed with water (10 mL), filtered and washed with CH$_2$Cl$_2$ (3×20 mL). Combined organic layers are dried over MgSO$_4$. Crude compound is purified by thick-layer chromatography (CH$_2$Cl$_2$/MeOH/NH$_4$OH: 80/20/0.9).
m/z (MALDI)=433.27
Compound is used as its oxalate salt

EXAMPLE 24

N$^4$-[3-(4-{3-[diisobutylamino]propyl}piperizano)propyl]-4-pyridinylmethylamine To a solution of the intermediate obtained in example 16 tetrahydrochlorhydride (150 mg, 0.48 mmol) in dry methanol (3 mL) 4-pyridinecarboxaldehyde (35 µL, 0.33 mmol) and 3 Å molecular sieves are added. The reaction media is stirred for 3 h, cooled to 0° C. NaBH$_4$ (75 mg, 1.97 mmol) is added portionwise for 30 min. After 1.5 h stirring, the reaction is hydrolysed with water (10 mL), filtered and washed with CH$_2$Cl$_2$ (3×20 mL). Combined organic layers are dried over MgSO$_4$. Crude compound is purified by thick-layer chromatography (CH$_2$Cl$_2$/NeOH/NH$_4$OH: 90/10/1.8).
m/z (MALDI)=404.2

EXAMPLE 25

Compound No. 9

N$^4$-[3-(4-{3-[diisobutylamino]propyl}piperizano)propyl]-4-fluorobenzylamine

To a solution of the intermediate obtained in example 16 (150 mg, 0.48 mmol) in dry ethanol (6 mL) 4-fluorobenzaldehyde (57 µL, 0.53 mmol) and 3 Å molecular sieves are added. The reaction media is stirred for 5 h, cooled to 0° C. NaBH$_4$ (46 mg, 1.2 mmol) is added portionwise. After 12 h stirring, the reaction was quentched by dropwise addition of water (10 mL) and ethanol was removed under reduced pressure. The aqueous residue was extracted with CH$_2$Cl$_2$. Combined organic layers were extracted with HCl 1M. The combined aqueous layers were neutralized with NaOH 1M and extracted with CH$_2$Cl$_2$. Combined organic layers were dried over MgSO$_4$. Crude compound is purified by thick-layer chromatography (CH$_2$Cl$_2$/MeOH/NH$_4$OH: 90/10/1).
m/z (MALDI) 421.4

EXAMPLE 26

N$^4$-[3-(4-{3-diisobutylamino]propyl}piperizano)propyl]-4-chlorobenzylamine

To a solution of the intermediate obtained in example 16 (150 mg, 0.48 mmol) in dry ethanol (6 mL) 4-chlorobenzaldehyde (74 mg, 0.53 mmol) and 3 Å molecular sieves are added. The reaction media is stirred for 5 h, cooled to 0° C. NaBH$_4$ (46 mg, 1.2 mmol) is added portionwise. After 12 h stirring, the reaction was quentched by dropwise addition of water (10 mL) and ethanol was removed under reduced pressure. The aqueous residue was extracted with CH$_2$Cl$_2$. Combined organic layers were extracted with HCl 1M. The combined aqueous layers were neutralized with NaOH 1M and extracted with CH$_2$Cl$_2$. Combined organic layers were dried over MgSO$_4$. Crude compound is purified by thick-layer chromatography (ethyl acetate/MeOH/NH$_4$OH: 90/10/2).
m/z (MALDI)=437.4

EXAMPLE 27

Compound No. 10

N$^4$-[3-(4-{3-[diisobutylamino]propyl}piperizano)propyl]-2-thiazolylmethylamine To a solution of the intermediate obtained in example 16 (150 mg, 0.48 mmol) in dry, ethanol (6 mL) 2-thiazolecarboxaldehyde (47 µL, 0.53 mmol) and 3 Å molecular sieves are added. The reaction media is stirred for 5 h, cooled to 0° C. NaBH$_4$ (46 mg, 1.2 mmol) is added portionwise. After 12 h stirring, the reaction was quentched by dropwise addition of water (10 mL) and ethanol was removed under reduced pressure. The aqueous residue was extracted with CH$_2$Cl$_2$. Combined organic layers were extracted with HCl 1M. The combined aqueous layers were neutralized with NaOH 1M and extracted with CH$_2$Cl$_2$. Combined organic layers were dried over MgSO$_4$. Crude compound is purified by thick-layer chromatography (ethyl acetate/MeOH/NH$_4$OH: 90/10/2).
m/z (MALDI)=410.4

EXAMPLE 28

N$^1$-[3-(4-(3-[(7-chloro-4-quinolyl)amino]propylpiperizano)propyl]-N$^1$-cyclopropyl-methylcyclopropane-1-carboxamide To a solution of compound of example 12 (150 mg, 0.36 mmol) in dry CH$_2$Cl$_2$ (4 mL), cyclopropanecarboxylic acid (50 µl, 0.54 mmol), HBTU (314 mg, 0.82 mmol), HOBT (112 mg, 0.82 mmol) and N,N-diisopropylethylamine (361 µL, 2.05 mmol) are added. The reaction media is stirred for 4 h, diluted with CH$_2$Cl$_2$ (15 mL) and washed with NaHCO$_3$ 1M (2×25 mL). Organic layer is dried over MgSO$_4$. Crude compound is purified by thick-layer chromatography (CH$_2$Cl$_2$/MeOH/NH$_4$OH: 90/10/0.9).

m/z (MALDI)=484.4

EXAMPLE 29

Tert-butyl-N-3-[[3-(4-3-[(7-chloro-4-quinolyl)amino]propylpiperazino) propyl](cyclopropylmethyl)amino]-3-oxopropylcarbamate To a solution of compound of example 12 (150 mg, 0.36 mmol) in dry CH$_2$Cl$_2$ (4 mL), Boc-β-alanine (102 mg, 0.54 mmol), HBTU (314 mg, 0.82 mmol), HOBT (112 mg, 0.82 mmol) and N,N-diisopropylethylamine (361 μL, 2.05 mmol) are added. The reaction media is stirred for 4 h, diluted with CH$_2$Cl$_2$ (15 mL) and washed with NaHCO$_3$ 1M (2×25 mL). Organic layer is dried over MgSO$_4$. Crude compound is purified by thick-layer chromatography (CH$_2$Cl$_2$/MeOH/NH$_4$OH: 90/10/0.9).

m/z (MALDI)=587.2

EXAMPLE 30

5-{[3-(4-[3-(7-chloro-4-quinolyl)amino]propylpiperazino)propyl](cyclo propylmethyl)amino}pentanenitrile A solution of compound of example 12 (150 mg, 0.36 mmol), 1-ethylpiperidine (247 μL, 1.8 mmol) and 5-chlorovaleronitrile (58 μL, 0.72 mmol) in acetonitrile (4 mL) was stirred at 40° C. for 6H. After evaporation, crude residue is solubilised in CH$_2$Cl$_2$ and washed with NaOH 1M. Organic layer is dried over MgSO$_4$. Crude compound is purified by thick-layer chromatography (CH$_2$Cl$_2$/MeOH/NH$_4$OH: 90/10/0.9).

m/z=497.5

EXAMPLE 31

Tert-butyl-N-3-{[3-(4-[3-(7-chloro-4-quinolyl)amino]propylpiperazino) propyl](cyclopropylmethyl)amino}propylcarbamate a) N-Boc-aminopropanal (Intermediate Synthesised in 2 Steps)

Step 1: Synthesis of N-Boc-aminopropan-3-ol

A solution of aminopropanol (1.02 mL, 13.3 mmol), Boc$_2$O (3.2 g, 14.6 mmol) in dioxane/NaOH 0.5 M: 1/1 (48.8 mL) was stirred overnight. After evaporations crude residue is solubilised in ethyl acetate and washed with citric acid. Organic layer is dried over MgSO$_4$ and evaporated to yield expected compound.

Step 2: Synthesis of the Intermediate

A solution of N-Boc-aminopropan-3-ol (0.5 g, 2.83 mmol) and PCC (pyridinium chlorochromate) (0.91 g, 4.24 mmol) in dry CH$_2$Cl$_2$ (15 mL) was stirred for 4 h. After evaporation, crude residue is purified by flash chromatography (cyclohexane/AcOEt:1/1) to yield expected compound as white powder.

b) Tert-butyl-N-3-{[3-(4-[3-(7-chloro-4-quinolyl)amino]propylpiperazino) propyl](cyclopropylmethyl)amino}propylcarbamate To a solution of N-Boc-aminopropanal (94 g, 0.54 mmol) and compound of example 12 (150 mg, 0.36 mmol) in dry CH$_2$Cl$_2$ (4 mL), NaHB(OAc)$_3$ (229 mg, 1.08 mmol) is added. The reaction media was stirred for 4 h and NaOH 1M (5 mL) is added. Organic layer is washed with NaOH 1M and dried over MgSO$_4$. Crude compound is purified by thick-layer chromatography (CH$_2$Cl$_2$/MeOH/NH$_4$OH: 80/20/0.9).

m/z (TOF)=573.3

EXAMPLE 32

Compound No. 11

1,4-bis(3-[diisobutylamino]propyl)piperazine

To a solution of 1,4-bis(3-aminopropyl)piperazine (200 mg, 1.0 mmol) in dry CH$_2$Cl$_2$ (15 mL) isobutyraldehyde (818 μL, 6.0 mmol) and NaHB(OAc)$_3$ (1.27 g, 6.0 mmol) are added. The reaction media is stirred for 4 h and NaOH 1M (25 mL) is added. Organic layer is separated and aqueous layer is washed with CH$_2$Cl$_2$. Combined organic layers are dried over MgSO$_4$. Crude compound is purified by thick-layer chromatography (CH$_2$Cl$_2$/MeOH/NH$_4$OH: 90/10/0.9).

m/z (MALDI)=425.4

EXAMPLE 33

Compound No. 12

1,4-bis(3-[dicyclopropylmethylamino]propyl)piperazine

To a solution of 1,4-bis(3-aminopropyl)piperazine (400 μL, 1.94 mmol) in dry CH$_2$Cl$_2$ (30 mL) cyclopropanecarboxaldehyde (871 μL, 11.6 mmol) and NaHB(OAc)$_3$ (2.47 g, 11.6 mmol) are added. The reaction media is stirred for 4 h and NaOH 1M (75 mL) is added. Organic layer is separated and aqueous layer is washed with CH$_2$Cl$_2$. Combined organic layers are dried over MgSO$_4$. Crude compound is purified by flash chromatography (CH$_2$Cl$_2$/MeOH/NH$_4$OH: 90/10/1).

m/z (MALDI)=417.4

EXAMPLE 34

Compound No. 13

1,4-bis{2-[4-chlorobenzyl)amino]ethyl}piperazine

To a solution of 1,4-bis(2-aminoethyl)piperazine (0.43 g, 2.5 mmol) and 4-chlorobenzaldehyde (737 mg, 5.24 mmol) in absolute ethanol (20 mL), 3 Å molecular sieves are added. After stirring the mixture at room temperature for 12 h, NaBH$_4$ (1.9 g, 49.92 mmol) was added portionwise and the mixture was stirred for 12 h at room temperature. The reaction was quenched by dropwise addition of water (20 mL) and ethanol was removed under reduced pressure. The aqueous residue was extracted with CH$_2$Cl$_2$ (3×30 mL). Combined organic layers were extracted with HCl 1M. The combined aqueous layers were neutralized with NaOH 1M and extracted with CH$_2$Cl$_2$. Combined organic layers were dried over MgSO$_4$. Crude compound is purified by thick-layer chromatography (CH$_2$Cl$_2$/MeOH: 80/20).
m/z (MALDI)=421.4

EXAMPLE 35

Compound No. 14

1,4-bis{2-[4-fluorobenzyl)amino]ethyl}piperazine

To a solution of 1,4-bis(2-aminoethyl)piperazine (0.43 g, 2.5 mmol) and 4-fluorobenzaldehyde (0.59 mL, 5.5 mmol) in absolute ethanol (20 mL), 3 Å molecular sieves are added. After stirring the mixture at room temperature for 5 h, NaBH$_4$ (0.47 g, 12.5 mmol) was added portionwise and the mixture was stirred for 12 h at room temperature. The reaction was quentched by dropwise addition of water (20 mL) and ethanol was removed under reduced pressure. The aqueous residue was extracted with CH$_2$Cl$_2$ (3×30 mL). Combined organic layers were extracted with HCl 1M. The combined aqueous layers were neutralized with NaOH 1M and extracted with CH$_2$Cl$_2$. Combined organic layers were dried over MgSO$_4$. Crude compound is purified by thick-layer chromatography (CH$_2$Cl$_2$MeOH: 80/20).
m/z (MALDI)=389.5

EXAMPLE 36

Compound No. 15

1,4-bis{4-[4-chlorobenzyl)amino]butyl}piperazine

To a solution of 1,4-bis(4-aminobutyl)piperazine (0.57 g, 2.5 mmol) and 4-chlorobenzaldehyde (737 mg, 5.24 mmol) in absolute ethanol (20 mL), 3 Å molecular sieves are added. After stirring the mixture at room temperature for 12 h, NaBH$_4$ (1.9 g, 49.92 mmol) was added portionwise and the mixture was stirred for 12 h at room temperature. The reaction was quentched by dropwise addition of water (20 mL) and ethanol was removed under reduced pressure. The aqueous residue was extracted with CH$_2$Cl$_2$ (3×30 mL). Combined organic layers were extracted with HCl 1M. The combined aqueous layers were neutralized with NaOH 1M and extracted with CH$_2$Cl$_2$. Combined organic layers were dried over MgSO$_4$. Crude compound is purified by thick-layer chromatography (CH$_2$Cl$_{21}$MeOH/NH$_4$OH: 80/20/0.9).
m/z (MALDI)=477.3

EXAMPLE 37

Compound No. 16

1,4-bis{4-[4-fluorobenzyl)amino]butyl}piperazine

To a solution of 1,4-bis(4-aminobutyl)piperazine (0.57 g, 2.5 mmol) and 4-fluorobenzaldehyde (0.59 mL, 5.5 mmol) in absolute ethanol (20 mL), 3 Å molecular sieves are added. After stirring the mixture at room temperature for 5 h, NaBH$_4$ (0.47 g, 12.5 mmol) was added portionwise and the mixture was stirred for 12 h at room temperature. The reaction was quentched by dropwise addition of water (20 mL) and ethanol was removed under reduced pressure. The aqueous residue was extracted with CH$_2$Cl$_2$ (3×30 mL). Combined organic layers were extracted with HCl 1M. The combined aqueous layers were neutralized with NaOH 1M and extracted with CH$_2$Cl$_2$. Combined organic layers were dried over MgSO$_4$. Crude compound is purified by thick-layer chromatography (CH$_2$Cl$_2$/MeOH/NH$_4$OH: 80/20/0.9).
m/z (MALDI)=445.6

EXAMPLE 38

N-(7-chloro-quinolin-4-yl)-N-3-[4-(3-pyrrolidin-1-yl-propyl)piperazin-1-yl]propylamine To a solution of 1,4-bis{3-[N-(7-chloroquinolin-4-yl)amino]propyl}piperazine described in example 1 (0.15 g, 0.41 mmol), 1,4-dibromobutane (0.06 mL, 0.5 mmol) in DMF (5 mL), K$_2$CO$_3$ (287 mg, 2.07 mmol) is added. After stirring the mixture at room temperature for 48 h, the solvent was removed under reduced pressure. The residue was solubilized in CH$_2$Cl$_2$, washed with NaHCO$_3$ 1M and dried over MgSO$_4$. Crude compound is purified by thick-layer chromatography (CH$_2$Cl$_2$/MeOH/NH$_4$OH: 80/20/2.7).
m/z (MALDI)=416.2

EXAMPLE 39

N-(7-chloro-quinolin-4-yl)-N-3-[4-(3-piperidin-1-yl-propyl)piperazin-1-yl]propylamine To a solution of 1,4-bis{3-[N-(7-chloroquinolin-4-yl)amino]propyl}piperazine described in example 1 (0.15 g, 0.41 mmol), 1,5-dibromopentane (0.068 mL, 0.5 mmol) in DMF (5 mL), K$_2$CO$_3$ (287 mg, 2.07 mmol) is added. After stirring the mixture at room temperature for 48 h, the solvent was removed under reduced pressure. The residue was solubilized in CH$_2$Cl$_2$, washed with NaHCO$_3$ 1M and dried over MgSO$_4$. Crude compound is purified by thick-layer chromatography (CH$_2$Cl$_2$/MeOH/NH$_4$OH: 80/20/2.7).
m/z (MALDI) 430.2

EXAMPLE 40

N-3-[4-(3-azepan-1-ylpropyl)piperazin-1-yl]propyl-N-(7-chloro-4-quinolyl)-amine

To a solution of 1,4-bis{3-[N-(7-chloroquinolin-4-yl)amino]propyl}piperazine described in example 1 (0.15 g, 0.41 mmol), 1,6-dibromohexane (0.077 mL, 0.5 mmol) in DMF (5 mL), K$_2$CO$_3$ (287 mg, 2.07 mmol) is added. After stirring the mixture at room temperature for 48 h, the solvent was removed under reduced pressure. The residue was solubilized in CH$_2$Cl$_2$, washed with NaHCO$_3$ 1M and dried over MgSO$_4$. Crude compound is purified by thick-layer chromatography (CH$_2$Cl$_2$/MeOH/NH$_4$OH: 80/20/2.7).
m/z (MALDI)=444.1

EXAMPLE 41

Compound No. 17

{3-[4-(3-Diisobutylamino-propyl)-piperazin-1-yl]-propyl}-(6-methyl-1H-benzimidazol-2-yl)-amine a) 1-{(3-[4(3-Diisobutylamino-propyl)-piperazin-1-yl]-propyl}-3-(4-methyl-2-nitro-phenyl)-thiourea (Intermediate)

A solution of N$^4$-(3-{4-[3-(diisobutylamino)propyl]piperizano}propyl)-amine (intermediate of example 16) (103 mg, 0.33 mmol) and 4-methyl-2-nitrophenyl isothiocyanate (128 mg, 0.66 mmol) in CH$_2$Cl$_2$ (10 mL) has been stirred for 4 h at room temperature. NaOH 1M is added until alkaline pH. Organic layer was washed with NaOH 0.5M and dried over MgSO$_4$. Crude compound is purified by thick-layer chromatography (CH$_2$Cl$_2$/MeOH: 90/10).

m/z (MALDI)=507.3 b) {3-[4-(3-Diisobutylamino-propyl)-piperazin-1-yl]-propyl}-(6-methyl-1H-benzimidazol-2-yl)-amine To a solution of thiourea (289 mg, 0.57 mmol) in absolute ethanol (13 mL), SnCl$_2$ (217 mg, 1.14 mmol) is added. After stirring the mixture at reflux for 24 h, the solvent was removed under reduced pressure. NaOH 1M (20 mL) was added and the aqueous layer was extracted several times with CH$_2$Cl$_2$. Combined organic layers were washed with brine and dried over MgSO$_4$. Crude compound is purified by flash chromatography (CH$_2$Cl$_2$/MeOH/NH$_4$OH: 90/10/0.2).

m/z (MALDI)=443.4

EXAMPLE 42

Compound No. 18

{3-[4-(3-Diisobutylamino-propyl)-piperazin-1-yl]-propyl}-(6-methoxy-1H-benzimidazol-2-yl)-amine a) 1-{3-[4-(3-Diisobutylamino-propyl)-piperazin-1-yl]-propyl}-3-(4-methoxy-2-nitro-phenyl)-thiourea (Intermediate)

A solution of N$^4$-(3-{4-[3-(diisobutylamino)propyl]piperizano}propyl)-amine (intermediate of example 16) (103 mg, 0.33 mmol) and 4-methoxy-2-nitrophenyl isothiocyanate (139 mg, 0.66 mmol) in CH$_2$Cl$_2$ (10 mL) has been stirred for 4 h at room temperature. NaOH 1M is added until alkaline pH. Organic layer was washed with NaOH 0.5M and dried over MgSO$_4$. Crude compound is purified by thick-layer chromatography (CH$_2$Cl$_2$/MeOH: 90/10).

m/z (MALDI)=523.3 b) {3-[4-(3-Diisobutylamino-propyl)-piperazin-1-yl]-propyl}-(6-methoxy-1H-benzimidazol-2-yl)-amine To a solution of thiourea (298 mg, 0.57 mmol) in absolute ethanol (13 mL), SnCl$_2$ (217 mg, 1.14 mmol) is added. After stirring the mixture at reflux for 24 h, the solvent was removed under reduced pressure. NaOH 1M (20 mL) was added and the aqueous layer was extracted several times with CH$_2$Cl$_2$. Combined organic layers were washed with brine and dried over MgSO$_4$. Crude compound is purified by flash chromatography (CH$_2$Cl$_2$/MeOH/NH$_4$OH: 90/10/0.2).

m/z (MALDI)=459.4

EXAMPLE 43

Compound No. 19

(1H-Benzimidazol-2-yl)-{3-[4-(3-pyrrolidin-1-yl-propyl)-piperazin-1-yl]-propyl}-amine a) {3-[4-(3-Amino-propyl)-piperazin-1-yl]-propyl}-(1H-benzimidazol-2-yl)-amine (Intermediate Synthesised in 3 Steps)

Step 1: Synthesis of [3-(4-{3-[3-(2-Nitro-phenyl)-thioureido]-propyl}-piperazin-1-yl)-propyl]-carbamic Acid Tert-Butyl Ester N-(3-{4-[3-(tert-butylcarbobenzyloxyamino)propyl]piperizano}propyl)amine (synthesized for example 16) (0.5 g, 1.17 mmol) was dissolved in freshly distilled CH$_2$Cl$_2$ (30 mL). 2-nitrophenylisothiocyanate (0.6 g, 3.33 mmol) was added by small portions. The resulting yellow solution was stirred for 4 h at room temperature. Then a sodium hydroxide solution 1.0M was added until pH 12-13. The organic layer was washed three times with a hydroxide sodium solution 0.5M (3×20 mL). It was then dried over anhydrous MgSO$_4$, filtered and concentrated under reduced pressure. The crude residue was purified by flash chromatography (AcOEt/MeOH:85/15).

m/z (MALDI)=481.4

Step 2: Synthesis of (3-{4-[3-(1H-Benzimidazol-2-ylamino)-propyl]-piperazin-1-yl}-propyl)-carbamic Acid Tert-Butyl Ester

[3-(4-[3-[3-(2-Nitro-phenyl)-thioureido]-propyl]-propyl]-carbamic acid tert-butyl ester (0.45 g, 0.93 mmol) was dissolved in absolute ethanol (50 mL) then anhydrous tin chloride (0.35 g, 1.87 mmol) was added. The solution was heated to reflux. After 48 h, the resulting mixture was cooled to room temperature. The solvent was removed under reduced pressure and the residue was dissolved in ethyl acetate (30 mL), adjusted until pH 8-9 with NaOH 1M and the organic layer was washed with water (3×25 mL). It was then dried over anhydrous MgSO$_4$, filtered and concentrated under reduced pressure. The crude residue was purified by flash chromatography (CH$_2$Cl$_2$/MeOH/NH$_4$OH 9/1/0.1).

m/z (MALDI)=417.4

Step 3: Synthesis of the Intermediate (3-[4-[3-(1H-Benzimidazol-2-ylamino)-propyl]-piperazin-1-yl]-propyl)-carbamic acid tert-butyl ester (0.2 g, 0.5 mmol) was dissolved in CH$_2$Cl$_2$ (20 mL). Trifluoroacetic acid (0.38 mL, 5 mmol) was then added and the reaction mixture was stirred overnight at room temperature. The solvent and excess TFA were removed under reduced pressure and the resulting solid was triturated in hexane and filtered.

m/z (MALDI)=317.3 b) (1H-Benzimidazol-2-yl)-{3-[4-(3-pyrrolidin-1-yl-propyl)-piperazin-1-yl]-propyl}-amine

[3-[4-(3-Amino-propyl)-piperazin-1-yl]-propyl]-(1H-benzimidazol-2-yl)-amine (intermediate) (65 mg, 0.021 mmol) was dissolved in anhydrous DMF (20 mL) in the presence of potassium carbonate (142 mg, 1.0 mmol). 1,4-dibromobutane (0.03 mL, 0.25 mmol) was added. The resulting mixture was stirred for 48 h at room temperature. The solution was filtered and the solvent was removed under reduced pressure.

m/z (MALDI)=371.3

EXAMPLE 44

Compound No. 20

(1H-Benzimidazol-2-yl)-{3-[4-(3-isobutylamino-propyl)-piperazin-1-yl]-propyl}-amine To a solution of [3-[4-(3-Amino-propyl)-piperazin-1-yl]-propyl]-(1H-benzimidazol-2-yl)-amine (Intermediate of example 44) (130 mg, 0.41 mmol) in CH$_2$Cl$_2$ (4 mL) isobutyraldehyde (62 μL, 0.46 mmol), triethylamine (26 μL, 0.16 mmol) and 3 Å molecular sieves are added. The reaction media is stirred for 3 h and cooled before NaBH$_4$ (78 mg, 2.05 mmol) is added portionwise over 30 min. Stirring is left for 1.5 h, water (10 mL) is added and the media is filtered. Compound is extracted with $CH_2Cl_2$ (3×20 mL). Combined organic layers are dried over $MgSO_4$. Crude compound is purified by thick-layer chromatography ($CH_2Cl_2$/MeOH/ $NH_4OH$: 90/10/1.2).

m/z (TOF)=433.3

EXAMPLE 45

Compound No. 21

1,4-bis{3-[N-(1H-Benzimidazol-2-yl)amino] propyl}piperazine a) 1,4-bis{3-[4-methoxy-2-nitro-phenyl)-thiourea] propyl}piperazine (Intermediate)

1,4-bis(3-aminopropyl)-piperazine (1.0 g, 5 mmol) was dissolved in freshly distilled $CH_2Cl_2$ (50 mL). 2-nitrophenyl-isothiocyanate (3.6 g, 20 mmol) was added by small portions. The resulting yellow solution was stirred for 4 h at room temperature. A sodium hydroxide solution 1M was added until pH 12-13. The organic layer was washed with a hydroxide sodium solution 0.5M (3×50 ml). It was then dried over anhydrous $MgSO_4$, filtered and concentrated under reduced pressure. The crude residue was purified by flash chromatography ($CH_2Cl_2$/MeOH: 9/1).

m/z (MALDI)=561.3 b) 1,4-bis{3-[N-(1H-Benzimidazol-2-yl)amino] propyl}piperazine

To a solution of bis-thiourea (0.5 g, 0.9 mmol) in absolute ethanol (50 mL), $SnCl_2$ (0.68 g, 3.6 mmol) is added. After 48 h, the resulting mixture was cooled to room temperature. The solvent was removed under reduced pressure and the residue was dissolved in ethyl acetate (30 mL), adjusted until pH 8-9 with NaOH 1M and the organic layer was washed with water (3×25 mL). It was then dried over anhydrous $MgSO_4$, filtered and concentrated under reduced pressure. The crude residue was purified by flash chromatography ($CH_2Cl_2$/MeOH/ $NH_4OH$: 9/1/0.1).

m/z (MALDI)=433.3

EXAMPLE 46

1,4-bis{3-[N-(anthr-9-ylmethyl)amino] propyl}piperazine

To a solution of 1,4-bis(3-aminopropyl)piperazine (0.513 mL, 2.49 mmol) and 9-anthracenaldehyde (1.080 g, 5.24 mmol) in absolute ethanol (20 mL) was added 3 Å molecular sieves (5 g). After stirring the mixture for 12 h at room temperature, sodium borohydride (1.9 g, 49.9 mmol) was added and the mixture was stirred for 12 h at room temperature. Then the reaction mixture was quenched by dropwise addition of water (20 mL) and ethanol was removed under reduced pressure. The aqueous residue was extracted with $CH_2Cl_2$ (3×30 mL) and the combined organic layers were extracted with HCl 1N (2×50 mL). The combined aqueous layers were neutralized with NaOH 1N (50 mL) and extracted with $CH_2Cl_2$ (3×30 mL). The combined organic layers were dried over $MgSO_4$, evaporated to dryness and the oily residue purified by flash chromatography (neutral aluminium oxide, $CH_2Cl_2$/MeOH: 90/10).

m/z (MALDI)=581.36

EXAMPLE 47

1,4-bis{3-[N-(Benzyl)amino]propyl}piperazine

To a solution of 1,4-bis(3-aminopropyl)piperazine (0.513 mL, 2.49 mmol) and benzaldehyde (0.532 mL, 5.24 mmol) in absolute ethanol (20 mL) was added 3 Å molecular sieves (5 g). After stirring the mixture for 12 h at room temperature, sodium borohydride (1.9 g, 49.9 mmol) was added and the mixture was stirred for 12 h at room temperature. Then the reaction mixture was quenched by dropwise addition of water (20 mL) and ethanol was removed under reduced pressure. The aqueous residue was extracted with $CH_2Cl_2$ (3×30 mL) and the combined organic layers were extracted with HCl 1N (2×50 mL). The combined aqueous layers were neutralized with NaOH 1N (50 mL) and extracted with $CH_2Cl_2$ (3×30 mL). The combined organic layers were dried over $MgSO_4$, evaporated to dryness and the oily residue purified by flash chromatography (neutral aluminium oxide, $CH_2Cl_2$/MeOH: 90/10).

m/z (MALDI)=381.3

EXAMPLE 48

1,4-bis{3-[N-(4-nitrobenzyl)amino] propyl}piperazine

To a solution of 1,4-bis(3-aminopropyl)piperazine (0.513 mL, 2.49 mmol) and 4-nitrobenzaldehyde (792 mg, 5.24 mmol) in absolute ethanol (20 mL) was added 3 Å molecular sieves (5 g). After stirring the mixture for 12 h at room temperature, sodium borohydride (1.9 g, 49.9 mmol) was added and the mixture was stirred for 12 h under reflux. Then the reaction mixture was quenched by dropwise addition of water (20 mL) and ethanol was removed under reduced pressure. The aqueous residue was extracted with $CH_2Cl_2$ (3×30 mL) and the combined organic layers were extracted with HCl 1N (2×50 mL). The combined aqueous layers were neutralized with NaOH 1N (50 mL) and extracted with $CH_2Cl_2$ (3×30 mL). The combined organic layers were dried over $MgSO_4$, evaporated to dryness and the oily residue purified by flash chromatography (neutral aluminium oxide, $CH_2Cl_2$/MeOH: 90/10).

m/z (MALDI)=471.3

EXAMPLE 49

1,4-bis{3-[N-(napht-2-ylmethyl)amino] propyl}piperazine

To a solution of 1,4-bis(3-aminopropyl)piperazine (0.513 mL, 2.49 mmol) and 2-naphtaldehyde (818 mg, 5.24 mmol) in absolute ethanol (20 mL) was added 3 Å molecular sieves (5 g). After stirring the mixture for 12 h at room temperature, sodium borohydride (1.9 g, 49.9 mmol) was added and the mixture was stirred for 12 h at room temperature. Then the reaction mixture was quenched by dropwise addition of water (20 mL) and ethanol was removed under reduced pressure. The aqueous residue was extracted with $CH_2Cl_2$ (3×30 mL) and the combined organic layers were extracted with HCl 1N (2×50 mL). The combined aqueous layers were neutralized with NaOH 1N (50 mL) and extracted with $CH_2Cl_2$ (3×30 mL). The combined organic layers were dried over MgSO$_4$, evaporated to dryness and the oily residue purified by flash chromatography (neutral aluminium oxide, CH$_2$Cl$_2$/MeOH: 90/10).

m/z (MALDI)=481.3

EXAMPLE 50

1,4-bis{3-[N-(4-phenylbenzyl)amino]propyl}piperazine

To a solution of 1,4-bis(3-aminopropyl)piperazine (0.513 mL, 2.49 mmol) and 4-phenylbenzaldehyde (955 mg, 5.24 mmol) in absolute ethanol (20 mL) was added 3 Å molecular sieves (5 g). After stirring the mixture for 12 h at room temperature, sodium borohydride (1.9 g, 49.9 mmol) was added and the mixture was stirred for 12 h at room temperature. Then the reaction mixture was quenched by dropwise addition of water (20 mL) and ethanol was removed under reduced pressure. The aqueous residue was extracted with CH$_2$Cl$_2$ (3×30 mL) and the combined organic layers were extracted with HCl 1N (2×50 mL). The combined aqueous layers were neutralized with NaOH 1N (50 mL) and extracted with CH$_2$Cl$_2$ (3×30 mL). The combined organic layers were dried over MgSO$_4$, evaporated to dryness and the oily residue purified by flash chromatography (neutral aluminium oxide, CH$_2$Cl$_2$/MeOH: 90/10).

m/z (MALDI)=533.4

EXAMPLE 51

1,4-bis{3-[N-(3,4-dibenzyloxybenzyl)amino]propyl}piperazine

To a solution of 1,4-bis(3-aminopropyl)piperazine (0.513 mL, 2.49 mmol) and 3,4-dibenzyloxybenzaldehyde (1.668 g, 5.24 mmol) in absolute ethanol (20 mL) was added 3 Å molecular sieves (5 g). After stirring the mixture for 12 h at room temperature, sodium borohydride (1.9 g, 49.9 mmol) was added and the mixture was stirred for 12 h at room temperature. Then the reaction mixture was quenched by dropwise addition of water (20 mL) and ethanol was removed under reduced pressure. The aqueous residue was extracted with CH$_2$Cl$_2$ (3×30 mL) and the combined organic layers were extracted with HCl 1N (2×50 mL). The combined aqueous layers were neutralized with NaOH 1N (50 mL) and extracted with CH$_2$Cl$_2$ (3×30 mL). The combined organic layers were dried over MgSO$_4$, evaporated to dryness and the oily residue purified by flash chromatography (neutral aluminium oxide, CH$_2$Cl$_2$/MeOH: 90/10).

m/z (MALDI)=805.5

EXAMPLE 52

1,4-bis{3-[N-(fluoren-2-ylmethyl)amino]propyl}piperazine

To a solution of 1,4-bis(3-aminopropyl)piperazine (0.513 mL, 2.49 mmol) and 2-fluorenecarboxaldehyde (1.018 g, 5.24 mmol) in absolute ethanol (20 mL) was added 3 Å molecular sieves (5 g). After stirring the mixture for 12 h at room temperature, sodium borohydride (1.9 g, 49.9 mmol) was added and the mixture was stirred for 12 h at room temperature. Then the reaction mixture was quenched by dropwise addition of water (20 mL) and ethanol was removed under reduced pressure. The aqueous residue was extracted with CH$_2$Cl$_2$ (3×30 mL) and the combined organic layers were extracted with HCl 1N (2 25×50 mL). The combined aqueous layers were neutralized with NaOH 1N (50 mL) and extracted with CH$_2$Cl$_2$ (3×30 mL). The combined organic layers were dried over MgSO$_4$, evaporated to dryness and the oily residue purified by flash chromatography (neutral aluminium oxide, CH$_2$Cl$_2$/MeOH: 90/10).

m/z (MALDI)=557.36

EXAMPLE 53

1,4-bis{3-[N-(benzofur-2-ylmethyl)amino]propyl}piperazine

To a solution of 1,4-bis(3-aminopropyl)piperazine (0.513 mL, 2.49 mmol) and benzo[b]furan-2-carboxaldehyde (565 mg, 5.24 mmol) in absolute ethanol (20 mL) was added 3 Å molecular sieves (5 g). After stirring the mixture for 12 h at room temperature, sodium borohydride (1.9 g, 49.9 mmol) was added and the mixture was stirred for 12 h at room temperature. Then the reaction mixture was quenched by dropwise addition of water (20 mL) and ethanol was removed under reduced pressure. The aqueous residue was extracted with CH$_2$Cl$_2$ (3×30 mL) and the combined organic layers were extracted with HCl 1N (2×50 mL). The combined aqueous layers were neutralized with NaOH 1N (50 mL) and extracted with CH$_2$Cl$_2$ (3×36 mL). The combined organic layers were dried over MgSO$_4$, evaporated to dryness and the oily residue purified by flash chromatography (neutral aluminium oxide, CH$_2$Cl$_2$/MeOH: 90/10).

m/z (MALDI)=461.3

EXAMPLE 54

1,4-bis{3-[N-(quinol-2-ylmethyl)amino]propyl}piperazine

To a solution of 1,4-bis(3-aminopropyl)piperazine (0.513 mL, 2.49 mmol) and 2-quinolinecarbaldehyde (823 mg, 5.24 mmol) in absolute ethanol (20 mL) was added 3 Å molecular sieves (5 g). After stirring the mixture for 12 h at room temperature, sodium borohydride (1.9 g, 49.9 mmol) was added and the mixture was stirred for 12 h at room temperature. Then the reaction mixture was quenched by dropwise addition of water (20 mL) and ethanol was removed under reduced pressure. The aqueous residue was extracted with CH$_2$Cl$_2$ (3×30 mL) and the combined organic layers were extracted with HCl 1N (2×50 mL). The combined aqueous layers were neutralized with NaOH 1N (50 mL) and extracted with CH$_2$Cl$_2$ (3×30 mL). The combined organic layers were dried over MgSO$_4$, evaporated to dryness and the oily residue purified by flash chromatography (neutral aluminium oxide, CH$_2$Cl$_2$/MeOH: 90/10).

m/z (MALDI)=483.3

The table which follows illustrates the chemical structures and the MWT of some compounds according to the invention.

TABLE I
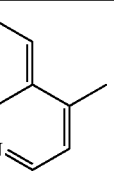
(I)
| Example | n | m | R₁ | R₂ | R₃ | R₄ | Salt | MWT |
|---|---|---|---|---|---|---|---|---|
| 1 | 3 | 3 | H | 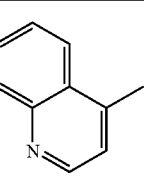 | H | 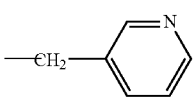 | — | 522.21 |
| 2 | 3 | 3 | H | 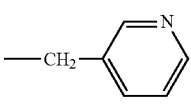 | H | 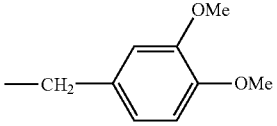 | 4 HCl | 526.19 |
| 3 | 3 | 3 | H | 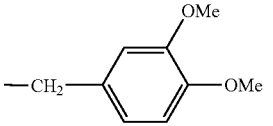 | H | 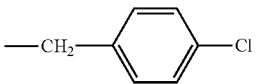 | 4 HCl | 644.24 |
| 4 | 3 | 3 | H | 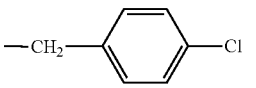 | H | 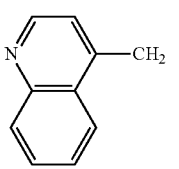 | 4 HCl | 592.12 |
| 5 (compound No. 1) | 3 | 3 | H | 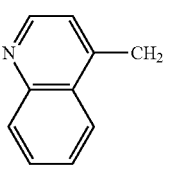 | H | 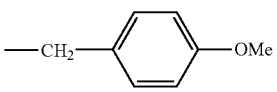 | 6 HCl | 698.18 |
| 6 (compound No. 2) | 3 | 3 | H | 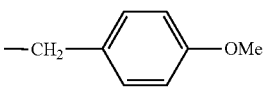 | H | 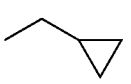 | 4 HCl | 584.22 |
| 7 | 3 | 3 | H | 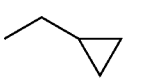 | H | 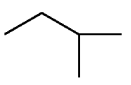 | 4 HCl | 452.20 |
| 8 (compound No. 3) | 3 | 3 | H | 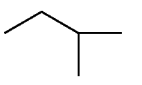 | H | 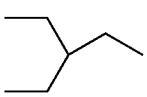 | 4 HCl | 456.23 |
| 9 (compound No. 4) | 3 | 3 | H | 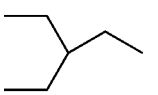 | H |  | 4 HCl | 512.29 |
| 10 (compound No. 5) | 3 | 3 | H | 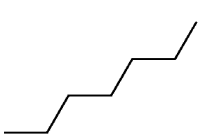 | H | 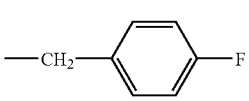 | 4 HCl | 540.33 |
| 11 (compound No. 6) | 3 | 3 | H | 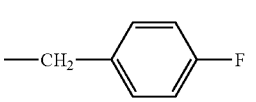 | H | | | 416.27 |

TABLE I-continued
(I)
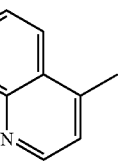
| Example | n | m | R₁ | R₂ | R₃ | R₄ | Salt | MWT |
|---|---|---|---|---|---|---|---|---|
| 12 | 3 | 3 | H | 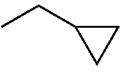 | H | 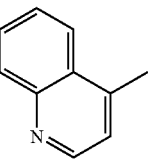 | — | 415.25 |
| 13 | 3 | 3 | H | 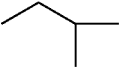 | H | 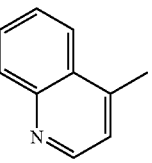 | — | 417.27 |
| 14 | 3 | 3 | H | 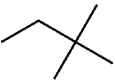 | H | 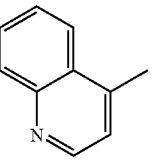 | — | 431.28 |
| 15 | 3 | 3 | H | 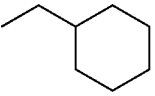 | H | 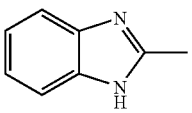 | — | 457.30 |
| 16 | 3 | 3 | H | 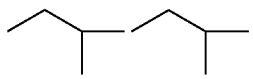 | 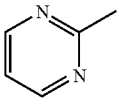 | | 2 COOH—COOH | 608.35 |
| 17 (compound No. 7) | 3 | 3 | H | 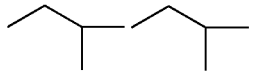 | 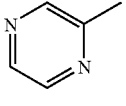 | | — | 390.35 |
| 18 | 3 | 3 | H | 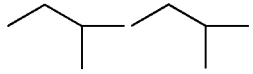 | 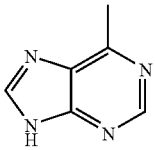 | | — | 390.35 |
| 19 | 3 | 3 | H | 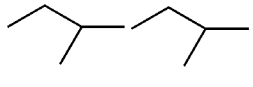 | 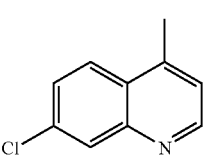 | | — | 430.35 |
| 20 | 3 | 3 | H | 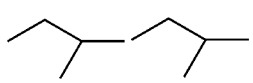 | | | — | 473.33 |

TABLE I-continued
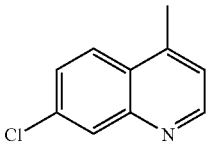
(I)
| Example | n | m | R₁ | R₂ | R₃ | R₄ | Salt | MWT |
|---|---|---|---|---|---|---|---|---|
| 21 | 3 | 3 | H | 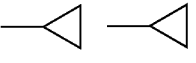 |  | 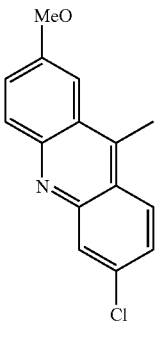 | — | 469.30 |
| 22 (compound No. 8) | 3 | 3 | H | 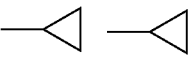 |  | 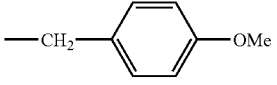 | — | 549.32 |
| 23 | 3 | 3 | H | 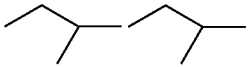 | 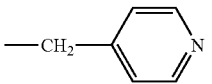 | | 2 COOH—COOH | 612.37 |
| 24 | 3 | 3 | H | 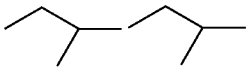 | 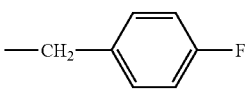 | | — | 403.37 |
| 25 (compound No. 9) | 3 | 3 | H | 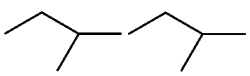 | 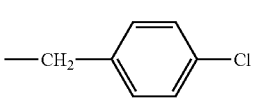 | | — | 420.36 |
| 26 | 3 | 3 | H | 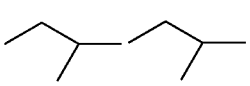 | 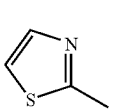 | | — | 436.33 |
| 27 (compound No. 10) | 3 | 3 | H | 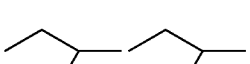 | 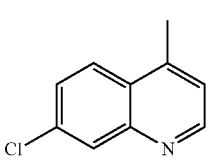 | | — | 409.32 |
| 28 | 3 | 3 | H | 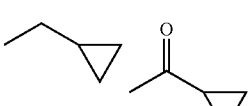 |  | 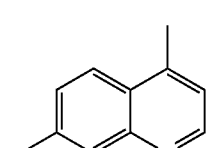 | — | 483.28 |
| 29 | 3 | 3 | H |  |  | | — | 586.34 |

TABLE I-continued
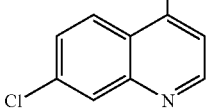
(I)
| Example | n | m | R₁ | R₂ | R₃ | R₄ | Salt | MWT |
|---|---|---|---|---|---|---|---|---|
| 30 | 3 | 3 | H |  | 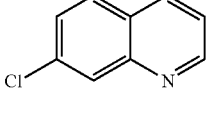 | —(CH₂)₄—CN | — | 496.31 |
| 31 | 3 | 3 | H |  | 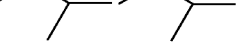 | —(CH₂)₃-A | — | 572.36 |
| 32 (compound No. 11) | 3 | 3 | 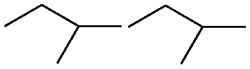 | |  | | — | 424.45 |
| 33 (compound No. 12) | 3 | 3 |  | |  | | — | 416.39 |
| 34 (compound No. 13) | 2 | 2 | H | 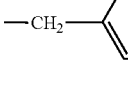 | H | 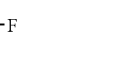 | 4 HCl | 564.09 |
| 35 (compound No. 14) | 2 | 2 | H | 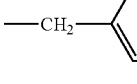 | H |  | 4 HCl | 532.15 |
| 36 (compound No. 15) | 4 | 4 | H | 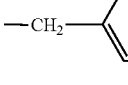 | H |  | 4 HCl | 620.15 |
| 37 (compound No. 16) | 4 | 4 | H | 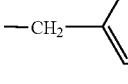 | H | 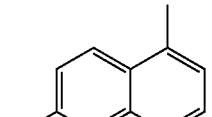 | 4 HCl | 588.22 |
| 38 | 3 | 3 | H |  | | 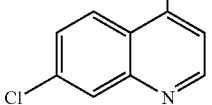 | — | 424.32 |
| 39 | 3 | 3 | H |  | | 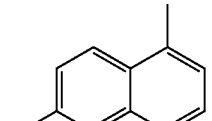 | — | 429.26 |
| 40 | 3 | 3 | H |  | | | — | 443.28 |

TABLE I-continued $$\text{R}_1\text{R}_2\text{N}-(\text{CH}_2)_n-\text{N}\underset{\underset{}{\bigcirc}}{}\text{N}-(\text{CH}_2)_m-\text{NR}_3\text{R}_4 \quad (I)$$

| Example | n | m | $R_1$ | $R_2$ | $R_3$ | $R_4$ | Salt | MWT |
|---|---|---|---|---|---|---|---|---|
| 41 (compound No. 17) | 3 | 3 | H | 5-methyl-2-methyl-benzimidazol-1-yl | H | 2,4-dimethylpentyl (branched) | — | 442.38 |
| 42 (compound No. 18) | 3 | 3 | H | 5-methoxy-2-methyl-benzimidazol-1-yl | H | 2,4-dimethylpentyl (branched) | — | 458.37 |
| 43 (compound No. 19) | 3 | 3 | H | 2-methylbenzimidazol-1-yl | \multicolumn{2}{c}{pyrrolidinyl} | — | 370.28 |
| 44 (compound No. 20) | 3 | 3 | H | 2-methylbenzimidazol-1-yl | H | sec-butyl | — | 372.30 |
| 45 (compound No. 21) | 3 | 3 | H | 2-methylbenzimidazol-1-yl | H | 2-methylbenzimidazol-1-yl | — | 432.27 |
| 46 | 3 | 3 | H | 9-anthrylmethyl | H | 9-anthrylmethyl | 4 HCl | 724.26 |
| 47 | 3 | 3 | H | benzyl | H | benzyl | 4 COOH—COOH | 740.28 |
| 48 | 3 | 3 | H | 4-nitrobenzyl | H | 4-nitrobenzyl | 4 COOH—COOH | 830.25 |
| 49 | 3 | 3 | H | 2-naphthylmethyl | H | 2-naphthylmethyl | — | 480.33 |
| 50 | 3 | 3 | H | 4-biphenylmethyl | H | 4-biphenylmethyl | 4 HCl | 676.26 |

TABLE I-continued $$\text{R}_1\text{R}_2\text{N}-(\text{CH}_2)_n-\text{N}\overset{\frown}{\underset{\smile}{\text{N}}}-(\text{CH}_2)_m-\text{NR}_3\text{R}_4 \quad (I)$$

| Example | n | m | R$_1$ | R$_2$ | R$_3$ | R$_4$ | Salt | MWT |
|---|---|---|---|---|---|---|---|---|
| 51 | 3 | 3 | H | 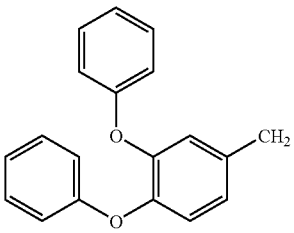  | H | 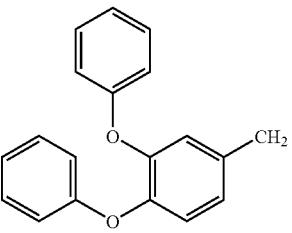 | 4 HCl | 948.37 |
| 52 | 3 | 3 | H | 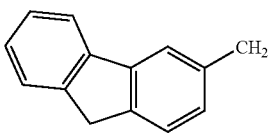 | H | 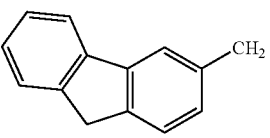 | 4 HCl | 700.26 |
| 53 | 3 | 3 | H | 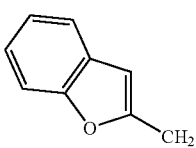 | H | 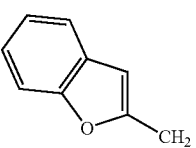 | 4 HCl | 604.19 |
| 54 | 3 | 3 | H | 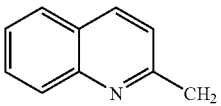 | H | 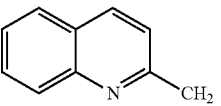 | 4 HCl | 626.22 |

In this table:
"-" represents a compound in free form,
Me represents a methyl group,
OMe represents a methoxy group,
A represents NHBoc with Boc being a tert-butoxycarbonyl group.
HCl represents a compound in a chlorhydrate form.

EXAMPLE 34

Pharmacological Test

The compounds of the invention have been the subject of pharmacological tests which have demonstrated their relevance as active substances in therapy and in particular in the treatment of neurodegenerative diseases.

Material and Methods
The Cell Line for Drug Screening
Cell Culture of Neuroblastoma SKNSH-SY5Y and Stable Transfection The human neuroblastoma cell line SH-SYSY were cultured in Dulbecco's modified Eagle medium supplemented with 10% fetal calf serum, 2 mM L-glutamine, 1 mM nonessential amino-acids, penicillin/streptomycin (Invitrogen SARL, Cergy Pontoise, France) and 200 µg/ml G418 (to select for APP expression) in a 5% $CO_2$ humidified incubator at 37° C. APP751 cDNA with the Swedish mutation (APP$^{Sw}$) was subcloned into stably eukaryotic expression vector pcDNA3 (Invitrogen), allowing for a G418 (Invitrogen) selection of stable clones. This APP cDNA was stably transfected into SH-SY5Y cells using the ethyleneimine polymer ExGen 500 (Euromedex) according to the manufacturer's instructions.

Drug Treatment of the Transfected Cell Line

Cells were plated into 6-well plates 24 h before drug exposure. Preceding the addition of drugs, cultures were washed once with warm phosphate-buffered saline (37° C.) and then exposed for 4, 8 or 24 h with drugs to be tested. After treatment, the medium was collected for the dosage of $A\beta_{1-42}$. Cells were washed with phosphate-buffered saline and scraped with a policeman rubber in 70 µl of Laemmli sample buffer with protease inhibitors (Complete Mini Roche Molecular Biochemicals, Meylan, France), sonicated and heat-treated for 5 min at 100° C. Protein concentration was established using the PlusOne™ 2-D Quant Kit (Amersham Biosciences, Orsay, France) and samples were kept at −80° C. until used.

Antibodies for the Quantification of APP-CTFs by Western Blots

The APPCter-C$_{17}$ antibody is raised against the last 17 amino acids of the human APP sequence (Sergeant, N., David, J. P., Champain, D., Ghestem, A., Wattez, A., and Delacourte, A. (2002) *J Neurochem* 81, 663-672). This polyclonal antibody detects all APP-CTFs fragments. The tubulin signal was used as a loading control and to normalize the APP-CTFs content. Anti-mouse or anti-rabbit secondary antibodies coupled with horseradish peroxidase were purchased at SIGMA Immunochemicals (Saint Quentin Fallavier, France).

Western Blotting

The same quantity of total proteins (20 μg/lane) was loaded on a 16.5% Tris-tricine polyacrylamide gel. Tris-tricine SDS-polyacrylamide gel electrophoresis (PAGE) was performed following the procedure of Schagger and Von Jagow (1987) (Schagger, H., and von Jagow, G. (1987) *Anal Biochem* 166, 368-379) with a protean II Xi Cell (Bio-Rad, Marnes la coquette, France). Proteins were transferred to nitrocellulose membrane at 2.5 mA/cm$^2$ per gel using the SemiDry Novablot Transfer system (Amersham Biosciences, Orsay, France), according to the manufacturer's instructions. Proteins were reversibly stained with Ponceau Red to check the quality of the transfer. Membranes were blocked in 25 mM Tris-HCl pH 8.0, 150 mM NaCl, 0.1% Tween-20 (v/v) and 5% (w/v) of skimmed milk for 30 min. Membranes were incubated overnight at 4° C. with appropriate dilutions of the primary antibodies, and incubated for 1 h at room temperature with secondary antibody. The immunoreactive complexes were revealed using the ECL™ Western Blotting kit (Amersham Biosciences) and Hyperfilms (Amersham Pharmacia Biotech).

Western blot films were digitized using an UMax scanner calibrated for optical densities (Amersham Biosciences). The Image-MASTER 1D ELITE Software (Amersham Biosciences) was used to quantify the signal, and data were collected using Excel Software (Microsoft, LesUlis, France).

Quantification of Secreted Aβ

The collected medium was spun at 200 g to eliminate the cell debris and Aβ$_{1-42}$ concentration was determined using the Innotest® β-Amyloid$_{1-42}$ (Innogenetics, Ghent, Belgium) according to the manufacturer's instructions.

Results

Impact of Drugs on the Levels of APP-CTFs α, β, γ Stubs and on the Resulting Aβ Peptide.

SKNSH SY5Y transfected cells were grown in the presence of drugs at different concentrations, for example at 1 μM or 5 μM, then cells were harvested and analyzed for their APP-CTF content, using the western-blot approach, while Aβ 1-42 of the cell supernatant was quantified by ELISA, as described in material and methods. For each compound, normal levels have the arbitrary value of 1. For example, if one APP-CTF is increased 10 times, the value is reported as 10. For Aβ peptide, if decreased of 60%, the value is reported as 0.4 (40% remaining).

FIG. 1 shows the results obtained for both compounds of the invention, the compound of example 4 and compound (5) of example 10. These results show that both compounds, compared to the control (i.e. without compound according to the invention), are efficient to decrease Aβ peptide levels at low concentration (1 μM) at 6 hours and that this efficiency is confirmed for a greater concentration (5 μM) at 24 hours. Furthermore, the compound of example 4 exhibits a particularly high efficiency for α and γ-APP-CTFs stubs (next table) as well for Aβ peptide (FIG. 1).

For the most active compounds, values for γ stubs were superior to 1 and in particular in the range 1 to 20; values for α stubs were superior to 1 and in particular in the range from 1 to 16 while the values for β stubs were inferior to 1 and in particular in the range from 0.4 to 1 and the values for Aβ peptide were inferior to 1 and in particular in the range from 0.1 to 1.

The table here-after submits data obtained for the compound of example 4 at two concentrations 1 μM and 5 μM, the values having been measured at 6 hours and 24 hours for each concentration.

|  | 6 h | | 24 h | |
| --- | --- | --- | --- | --- |
|  | 1 μM | 5 μM | 1 μM | 1 μM |
| β | 0.8 | 1.2 | 0.8 | 5 |
| α | 14 | 11 | 3.5 | 7 |
| γ | 9.6 | 5.7 | 5.1 | 14.4 |
| CTFs | 6 | 5 | 3.5 | 65 |
| Aβ | 0.2 | 0 | 1 | 0.1 |

Screening of the Molecules Through the Blood-Brain Barrier

The ability of some compounds to cross the Blood-Brain Barrier (BBB) has been evaluated, using an in vitro model (Cecchelli, R., et al., *In vitro model for evaluating drug transport across the blood-brain barriers*. Adv Drug Deliv Rev, 1999. 36(2-3): p. 165-178). The described model consists in brain capillary endothelial cells co-cultured with glial cells, thereby closely mimicking the in vivo conditions (Lundquist, S, and M. Renftel, *The use of in vitro cell culture models for mechanistic studies and as permeability screens for the blood-brain barrier in the pharmaceutical industry-background and current status in the drug discovery process*. Vascul Pharmacol 2002. 38(6): p. 355-64) and developed by CELLIAL Technologies SA.

For instance, examples 16 and 23 were soluble, able to diffuse across the filter membrane coated with collagen and without cells, and were not toxic on the endothelial cell monolayer at a concentration of 10 μM. The transport of drug was good for example 16 and moderate for example 23. Indeed, the permeability coefficients obtained for example 16 ($2.26 \times 10^{-3}$ cm/min) and example 23 ($1.81 \times 10^{-3}$ cm/min) indicate that these compounds cross the BBB and are good candidates as CNS drugs.

It is reminded here that from the literature, a good anti-Alzheimer compound should increase the levels of γ stubs that have a potential physiological role for the transcription of genes (Cao, X. and T. C. Sudhof, A transcriptively active complex of APP with Fe65 and histone acetyltransferase tip60. Science, 2001. 293(5527): p. 115-20; Pardossi-Piquard, R., et al., Presenilin-dependent transcriptional control of the Abeta-degrading enzyme neprilysin by intracellular domains of betaAPP and APLP. Neuron, 2005. 46(4): p. 541-54). Increased levels of α stubs are also expected, because the α cleavage is in competition with the β cleavage involved in the generation of AO species (Lichtenthaler S. F. and Haass C. (2004) Amyloid at the cutting edge: activation of α-secretase prevents amyloidogenesis in an Alzheimer disease mouse model. J Clin Invest 113, 1384-1387). The β cleavage that generates the β stub should be either normal or decreased. Aβ peptide, which is a potential neurotoxic, should be decreased. Together, a good anti-Alzheimer compound should in priority increased the levels of α and γ stubs and simultaneously decreased the Aβ peptide.

Therefore, the result of the tests carried out on the compounds disclosed in the present invention show that, in vitro, they exhibit the property to rectify the Amyloid Protein Precursor metabolism.

For this purpose an effective amount of a said compound may be administered to a subject suffering from a neurodegenerative disease or more generally to a subject suffering from a pathology linked to a metabolic defect of the APP protein. Among said neurodegenerative disease, Alzheimer's disease, Down syndrome, amyloid angiopathies, dementia with Lewy bodies and Parkinson's disease may be cited. The results also suggest that the compounds can be used for the treatment of cancer. Said compounds may also be used for diagnostic purposes.

More particularly, compounds of formula (I) containing a radiolabelled fluorine atom may be used as a medical imaging agent in particular or a metabolic marker, for example in the usual techniques in the medical field such as Position Emission Tomography (PET).

Among said compounds containing a fluorine atom, compounds Nos. 11 and 25 of the table may be cited, which necessitate a radiolabelling step in their synthesis.

Therefore the present invention is also related to the use of a compound of formula (I) including a marker system, for instance a radiolabelled fluorine atom, for the manufacture of a medical imaging agent intended for the diagnostic in the human being of a pathological or non pathological status, linked with a modification of the metabolism of Amyloid Protein Precursor (APP) or APP-like proteins, and in particular to neurodegenerative troubles.

The present invention also encompasses compositions for medical diagnostic containing a compound of formula (I) characterized in that said compound of formula (I) including a marker system, for instance a radiolabelled fluorine atom.

A further object of the invention relates to a compound of formula (II) according to the invention or anyone of the individual compounds (1) to (21) listed above for use as a medicament.

According to another of its aspects, the present invention relates to pharmaceutical compositions containing an active ingredient, chosen among a compound of formula (II) according to the invention and anyone of the individual compounds (1) to (21) listed above, their salts with pharmaceutically acceptable acids and mixture thereof.

Thus, these pharmaceutical compositions contain an effective amount of said compound, and one or more pharmaceutical excipients.

The aforementioned excipients are selected according to the dosage form and the desired mode of administration.

In this context they can be present in any pharmaceutical form which is suitable for enteral or parenteral administration, in association with appropriate excipients, for example in the form of plain or coated tablets, hard gelatin and other capsules, suppositories, or drinkable or injectable solutions or suspensions, in doses which enable the daily administration of from 0.1 to 1000 mg of active substance.

The present invention according to another of its aspects, also relates to a method of treatment of pathologies above indicated which comprises administering to a subject an effective amount of a compound according to formulae (I) or (II) or anyone of the individual compound (1) to (21) according to the invention or one of its pharmaceutically acceptable salts.

The invention claimed is:

1. A method of treating neurodegenerative diseases in which a dysfunction of the Amyloid Protein Precursor (APP) metabolism occurs, comprising:

administering at least a compound of formula (I)

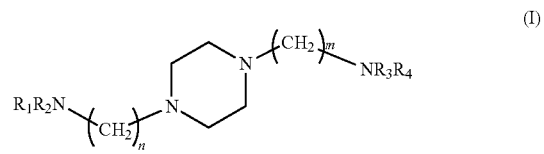

in which n and m are identical or different and independently represent an integer of greater than or equal to 2, the resulting hydrocarbon chain optionally comprising one or more heteroatoms selected from the group consisting of oxygen, nitrogen and sulphur, and, in which $R_1$, $R_2$, $R_3$ and $R_4$, independently of each other, are selected from the group consisting of:
   a hydrogen atom,
   a ($C_1$-$C_7$)alkyl group, straight or branched, saturated or unsaturated,
   an aryl group,
   an aralkyl group, where the aryl group is attached to a ($C_1$-$C_7$)alkylene bridging moiety, and
   a heteroaryl group,
   where ($R_1$ and $R_2$) and ($R_3$ and $R_4$) are different,
   where each ($C_1$-$C_7$)alkyl group is optionally substituted by one or more identical or different groups chosen from the group consisting of a halogen, a cyano group, a hydroxy group, a nitro group, an amino group, a ($C_1$-$C_7$) alkylamino group, a ($C_1$-$C_4$)alkoxy group, a tertbutoxycarbonylamino group, a HO—($C_1$-$C_8$)alkyl- group, a $H_2N$—($C_1$-$C_8$)alkyl- group, a HO—(C=O)— group, a ($C_1$-$C_8$)alkyl-O—(C=O)— group, a ($C_1$-$C_8$)alkyl-(C=O)— group, a ($C_1$-$C_8$)alkyl-(C=O)—($C_1$-$C_8$) alkyl- group, a $HSO_3$($C_1$-$C_8$)alkyl- group, a $H_2N$—(C=O)— group and a $H_2N$—(C=O)—($C_1$-$C_8$)alkyl- group,
   where the aryl group is selected from the group consisting of benzyl, phenyl, biphenyl, anthryl, phenylbenzyl, fluorenyl, naphthyl, dihydronaphthyl, tetrahydronaphthyl, indenyl and indanyl,
   where the heteroaryl group is selected from the group consisting of an aromatic monocycle, an aromatic bicycle, an aromatic tricycle and a bicycle or a tricycle of which one or two of the cycles is aromatic and the other cycle(s) is or are partially hydrogenated, from $C_5$ to $C_{14}$ comprising within the cyclic system one, two or three heteroatoms, identical or different, selected from the group consisting of oxygen, nitrogen and sulphur, and where each one of these aryl or heteroaryl groups optionally comprises one or more substitutions, identical or different, chosen from the group consisting of a halogen, a hydroxy group, a ($C_1$-$C_7$)alkyl group, a ($C_1$-$C_7$)alkoxy group, a ($C_7$-$C_{13}$)arylalkoxy group, a cyano group, a nitro group, an amino group, a ($C_1$-$C_7$)alkylamino group, a HO—($C_1$-$C_8$)alkyl- group, a $H_2N$—($C_1$-$C_8$)alkyl- group, a HO—(C=O)— group, a ($C_1$-$C_8$) alkyl-O—(C=O)— group, a ($C_1$-$C_8$)alkyl-(C=O)— group, a ($C_1$-$C_8$)alkyl-(C=O)—($C_1$-$C_8$)alkyl- group, a $HSO_3$($C_1$-$C_8$)alkyl-group, a $H_2N$—(C=O)— group and a $H_2N$—(C=O)—($C_1$-$C_8$)alkyl- group,
   where ($R_1$ and $R_2$) and/or ($R_3$ and $R_4$), independently of one another, optionally form an aromatic or partially or totally hydrogenated $C_4$ to $C_{14}$ monocycle, optionally comprising within the cyclic system one, two or three heteroatoms, identical or different, selected from the group consisting of oxygen, nitrogen and sulphur, provided that at most two of the radicals chosen among $R_1$, $R_2$, $R_3$ and $R_4$ simultaneously represent a hydrogen atom and that ($R_1$ and $R_2$) or ($R_3$ and $R_4$) do not simultaneously represent a hydrogen atom, or their salts with pharmaceutically acceptable acids.

2. The method according to claim 1, wherein n is ranging from 2 to 8.

3. The method according to claim 1, wherein n and m are identical.

4. The method according to claim 1, wherein n and m are equal to 2, 3 or 4.

5. The method according to claim 1, wherein the compound of formula (I) is such that $R_1$ and $R_3$ are hydrogen atoms and $R_2$ and $R_4$ are different and do not represent a hydrogen atom.

6. The method according to claim 5, wherein $R_2$ is a heteroaryl group and $R_4$ is a ($C_1$-$C_7$)alkyl group.

7. The method according to claim 1, wherein the compound of formula (I) is such that $R_1$ is a hydrogen atom, $R_2$ is different from a hydrogen atom and $R_3$ and $R_4$ are identical and different from a hydrogen atom.

8. The method according to claim 7, wherein $R_3$ and $R_4$ represent a ($C_1$-$C_7$)alkyl group or form with the nitrogen atom a saturated or unsaturated heterocycle, and $R_2$ represents a group chosen in the group consisting of:
- a benzimidazolyl group,
- a pyrimidinyl group,
- a pyrazinyl group,
- a purinyl group,
- a quinolinyl group,
- a chloroquinolinyl group,
- an acridinyl group,
- a benzyl group optionally substituted one or several times on the phenyl group by a group chosen from the group consisting of an atom of halogen and a methoxy group,
- a pyridinylmethyl group and,
- a thiazolylmethyl group.

9. The method according to claim 1, wherein the compound of formula (I) is such that $R_1$ is a hydrogen atom and $R_2$, $R_3$ and $R_4$ are different from each other and do not represent an hydrogen atom.

10. The method according to claim 1, wherein said compound is selected from the group consisting of:
- $N^4$-[3-(4-{3-[(cyclopropylmethyl)amino]propyl}piperazino)propyl]-7-chloroquinolin-4-amine,
- $N^4$-[3-(4-{3-(isobutylamino)propyl}piperazino)propyl]-7-chloroquinolin-4-amine,
- $N^4$-[3-(4-{3-(tert-pentylamino)propyl}piperazino)propyl]-7-chloroquinolin-4-amine,
- $N^4$-[3-(4-{3-(cyclohexylmethylamino)propyl}piperazino)propyl]-7-chloroquinolin-4-amine,
- $N^4$-(3-{4-[3-(diisobutylamino)propyl]piperazino}propyl)-benzimidazol-2-amine,
- $N^4$-(3-{4-[3-(diisobutylamino)propyl]piperazino}propyl)-pyrimidin-2-amine,
- $N^4$-(3-{4-[3-(diisobutylamino)propyl]piperazino}propyl)-pyrazin-2-amine,
- $N^4$-(3-{4-[3-(diisobutylamino)propyl]piperazino}propyl)-purine-6-amine,
- $N^4$-[3-{4-[3-(diisobutylamino)propyl]piperazino}propyl)-7-chloroquinolin-4-amine,
- $N^4$-[3-(4-{3-[di(cyclopropylmethyl)amino]propyl}piperazino)propyl]-7-chloroquinolin-4-amine,
- $N^4$-[3-(4-{3-[di(cyclopropylmethyl)amino]propyl}piperazino)propyl]-6-chloro-2-methoxyacridin-9-amine,
- $N^4$-[3-(4-{3-[diisobutylamino]propyl}piperazino)propyl]-4-benzyloxyamine,
- $N^4$-[3-(4-{3-[diisobutylamino]propyl}piperazino)propyl]-4 pyridinylmethylamine,
- $N^4$-[3-(4-{3-[diisobutylamino]propyl}piperazino)propyl]-4-fluorobenzylamine,
- $N^4$-[3-(4-{3-diisobutylamino]propyl}piperazino)propyl]-4-chlorobenzylamine,
- $N^4$-[3-(4-{3-[diisobutylamino]propyl}piperazino)propyl]-2-thiazolylmethylamine,
- $N^1$-[3-(4-3-[(7-chloro-4-quinoyl)amino]propylpiperazino)propyl]-N1-cyclopropyl-methylcyclopropane-1-carboxamide,
- Tert-butyl-N-3-[[3-(4-3-[(7-chloro-4-quinolyl)amino]propylpiperazino)propyl](cyclopropylmethyl)amino]-3-oxopropylcarbamate,
- 5-{[3-(4-[3-(7-chloro-4-quinolyl)amino]propyl piperazino)propyl](cyclopropylmethyl)amino}pentanenitrile,
- Tert-butyl-N-3-{[3-(4-[3-(7-chloro-4-quinolyl)amino]propyl piperazino)propyl](cyclopropylmethyl)amino}propylcarbamate,
- N-(7-chloro-quinolin-4-yl)-N-3-[4-(3-pyrrolidin-1-yl-propyl)piperazin-1-yl]propylamine,
- N-(7-chloro-quinolin-4-yl)-N-3-[4-(3-piperidin-1-yl-propyl)piperazin-1-yl]propylamine,
- N-3-[4-(3-azepan-1-ylpropyl)piperazin-1-yl]propyl-N-(7-chloro-4-quinolyl)-amine,
- {3-[4-(3-Diisobutylamino-propyl)-piperazin-1-yl]-propyl}-(6-methyl-1H-benzimidazol-2-yl)-amine,
- {3-[4-(3-Diisobutylamino-propyl)-piperazin-1-yl]-propyl}-(6-methoxy-1H-benzimidazol-2-yl)-amine,
- (1H-Benzimidazol-2-yl)-{3-[4-(3-pyrrolidin-1-yl-propyl)-piperazin-1-yl]-propyl}-amine, and
- (1H-Benzimidazol-2-yl)-{3-[4-(3-isobutylamino-propyl)-piperazin-1-yl]-propyl}-amine.

11. The method according to claim 1, wherein the neurodegenerative diseases in which a dysfunction of the Amyloid Protein Precursor (APP) metabolism occurs are chosen from Alzheimer's disease, Down syndrome, amyloid angiopathies, dementia with Lewy bodies and Parkinson's disease.

12. The method according to claim 6, wherein $R_2$ is 7-chloroquinolin-4-yl and $R_4$ is a cyclopropylmethyl group, an isobutyl group, a tertiobutylmethyl group or a cyclohexylmethyl group.

* * * * *